(12) United States Patent
Akiyama et al.

(10) Patent No.: US 7,250,488 B1
(45) Date of Patent: Jul. 31, 2007

(54) TRANSCRIPTIONAL ACTIVATION INHIBITORY PROTEIN

(75) Inventors: Tetsu Akiyama, Tokyo (JP); Tsutomu Nakamura, Saitama (JP); Kenichi Tago, Gunma (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 09/959,474

(22) PCT Filed: Apr. 26, 2000

(86) PCT No.: PCT/JP00/02727

§ 371 (c)(1), (2), (4) Date: Feb. 28, 2002

(87) PCT Pub. No.: WO00/64933

PCT Pub. Date: Nov. 2, 2000

(30) Foreign Application Priority Data

Apr. 27, 1999 (JP) ................................. 11-120266

(51) Int. Cl.
*C07K 5/00* (2006.01)
(52) U.S. Cl. ..................................................... 530/300
(58) Field of Classification Search ................ 530/350; 514/2
See application file for complete search history.

(56) References Cited

U.S. PATENT DOCUMENTS 5,851,775 A * 12/1998 Barker et al. ................... 435/6

FOREIGN PATENT DOCUMENTS

WO        WO 99 42481 A        8/1999

OTHER PUBLICATIONS

Tago et al., (Jul. 15, 2000, vol. 14, No. 14, pp. 1741-1749).*
Gura (Science, 1997, 278:1041-1042).*
Jain (Sci. Am., 1994, 271:58-65).*
Curti (Crit. Rev. in Oncology/Hematology, 1993, 14:29-39).*
Sakanaka et al., (Mar. 1998, Proc. Natl. Acad. Sci. USA, vol. 95, pp. 3020-3023).*
Hartwell et al (Science, 1997, 278:1064-1068).*
Hart et al., "Downregulation of β-Catenin by Human Axin and its Association with the APC Tumor Suppressor, β-Catenin and GSK3β," Research Papers, Current Biology, vol. 8, No, 10, Current Biology Ltd., pp. 573-581, 1998.
Ikeda et al., "Axin, a Negative Regulator of the Wnt Signaling Pathway, Forms a Complex with GSK-3β and β-Catenin and Promotes GSK-3β-Dependent Phosphorylation of β-Catenin," The EMBO Journal, vol. 17, No. 5, Oxford University Press, pp. 1371-1384, 1998.
Zheng et al., "The Mouse Fused Locus Encodes Axin, an Inhibitor of the Wnt Signaling Pathway That Regulates Embryonic Axis Formation," Cell, vol. 90, Cell Press, pp. 181-192, Jul. 11, 1997.
Rubinfeld et al., "Stabilization of β-Catenin by Genetic Defects in Melanoma Cell Lines," Science, vol. 275, pp. 1790-1792, Mar. 21, 1997.
Morin et al., "Activation of β-Catenin-Tcf Signaling in Colon Cancer by Mutations in β-Catenin or APC," Science, vol. 275, pp. 1787-1790, Mar. 21, 1997.
Korinek et al., "Constitutive Transcriptional Activation by a β-Catenin-Tcf Complex in APC$^{-/-}$ Colon Carcinoma," Science, vol. 275, pp. 1784-1787, Mar. 21, 1997.
Cadigan et al., "Wnt Signaling: A Common Theme in Animal Development," Genes & Development, vol. 11, Cold Spring Harbor Laboratory Press, pp. 3286-3305, 1997.
Rubinfeld et al., "Loss of β-Catenin Regulation by the APC Tumor Suppressor Protein Correlates with Loss of Structure Due to Common Somatic Mutations of the Gene[1]," Cancer Research, vol. 57, Onyx Pharmaceuticals, pp. 4624-4630, Oct. 15, 1997.
Nakamura et al., "Axin, an Inhibitor of the Wnt Signaling Pathway, Interacts with β-Catenin, GSK-3β and APC and Reduces the β-Catenin Level," Genes to Cells, vol. 3, Blackwell Science Limited, pp. 395-403, 1998.
Munemitsu et al., "Regulation of Intracellular β-Catenin Levels by the Adenomatous Polyposis Coli (APC) Tumor-Suppressor Protein," Proc. Natl. Acad. Sci. USA, vol. 92, Biochemistry, pp. 3046-3050, Mar. 1995.
Matsumine et al., "Binding of APC to the Human Homolog of the Drosophila Discs Large Tumor Suppressor Protein," Science, vol. 272, pp. 1020-1023, May 17, 1996.
Rubinfeld et al., "Binding of GSK3β to the APC-β-Catenin Complex and Regulation of Complex Assembly," Science, vol. 272, pp. 1023-1026, May 17, 1996.
Su et al., "Association of the APC Tumor Suppressor Protein with Catenins," Science, vol. 262, pp. 1734-1737, Dec. 10, 1993.
Rubinfeld et al., "Association of the APC Gene Product with β-Catenin," Science, vol. 262, pp. 1731-1734, Dec. 10, 1993.
Kinzler et a., "Lessons from Hereditary Colorectal Cancer," Cell, vol. 87, Cell Press, pp. 159-170, Oct. 18, 1996.
Kishida, S et al., "Axin, a negative regulatory of the Wnt signaling pathway, directly interacts with adenomatous polyposis coli and regulates the stabilization of β-catenin", J. Biol. Chem. (1998), vol. 273, No. 18, pp. 10823-10826.
Database EMBL, Dec. 23, 1999; Database Accession No. AI765102 XP002215647.
Database EMBL, Apr. 19, 2000, Database Accession No. AW702176 XP002215646.
Database NCBI, Feb. 10, 1999, Database Accession No. AI430277 XP002215645.
Database NCBI, Aug. 9, 1996, Database Accession No. AA0023778 XP002215644.
Sekiya, T. et al, Overexpression of *Icet* Induces $G_2$ Arrest and Cell Death in Tumor Cell Mutants for *Adenomatour Polyposis Coli, β-catenin*, or *Axin*; Cancer Research, Jun. 1, 2002, pp. 3322-3326; 62; Institute of Molecular and Cellular Biosciences, The University of Tokyo, Japan.

* cited by examiner

*Primary Examiner*—Misook Yu
(74) *Attorney, Agent, or Firm*—Foley & Lardner LLP

(57) ABSTRACT

A protein binding to β-catenin and thus inhibiting the transcriptional activation induced by the formation of a complex of β-catenin with a protein belonging to the TCF/Lef family; a DNA encoding this protein; an antibody recognizing this protein; a therapeutic agent containing the above protein or DNA; and a diagnostic agent containing the above antibody.

4 Claims, 6 Drawing Sheets

Mouse brain  Primary antibody : Anti-β-catenin antibody
Immunoprecipitation : Anti-ICAT antibody  Anti-β-catenin antibody

- 111
- 83

ICAT/COS7  Primary antibody : Anti-ICAT antibody
Immunoprecipitation : Anti-ICAT antibody  Anti-β-catenin antibody

- 8.2

Mouse brain  Primary antibody : Anti-TCF-4 antibody
Immunoprecipitation : Anti-ICAT antibody

- 83

TRANSCRIPTIONAL ACTIVATION INHIBITORY PROTEIN

TECHNICAL FIELD

The present invention relates to a protein having activities to bind to β-catenin and to inhibit transcriptional activation induced by formation of a complex of β-catenin with a protein belonging to the TCF/Lef family, a DNA encoding the protein, an antibody recognizing the protein, a therapeutic agent containing the protein or the DNA, and a diagnostic agent containing the antibody.

BACKGROUND ART

The abbreviations shown below are used herein.

AD: transcriptional activation domain

ADH: alcohol dehydrogenase

APC: adenomatous poliposis coli

BD: DNA-binding domain

β-catenin/TCF-4: complex between β-catenin and TCF-4

DCC: deleted in colorectal cancer dhfr: dihydrofolate reductase

DLG: *Drosophila* Discs Large

DMSO: dimethylsulfoxide

EGTA: ethylenediaminetetraacetic acid

ELISA: enzyme-linked immunosorbent assay

EST: expressed sequence tag

FAP: familial adenomatous poliposis

FCS: fetal calf serum

FITC: fluorescein isothiocyanate

GST: glutathione S-transferase

GST/ICAT: fusion protein between GST and ICAT

GSK-3β: glycogen synthase kinase-3β

ICAT: inhibitor of β-catenin and TCF

IPTG: isopropylthiogalactoside

KLH: keyhole limpet hemocyanin

Lef: lymphocyte enhancer-binding factor

LTR: long terminal repeat

MBS: m-maleimidobenzoyl-N-hydoroxysuccinimide

MEM: minimum essential medium

PCR: polymerase chain reaction

PEG: polyethylene glycol

RITC: rhodamine isothiocyanate

SDS: sodium dodecyl sulfate

SDS-PAGE: SDS-polyacrylamide gel electrophoresis

TCF: T cell factor

Tris: tris (hydroxymethyl) aminomethane

X-gal: 5-bromo-4-chloro-3-indolyl-β-D-galactoside

The APC gene was isolated as a causative gene of FAP (Kinzler and Vogelstein Cell, 87, 159 (1996)). However, it has been reported that the abnormality of the APC gene is observed not only in FAP but also in 70 to 80% cases of sporadic colon cancer. The onset of colon cancer have been considered to result from successive mutations in many genes including K-ras, p53, DCC and others as well as APC. Mutations are found at the earliest stage in the APC gene as compared with other genes, and thus it has been believed that the abnormality of the APC gene is a primary event for the onset of colon cancer.

In order to clarify the mechanism underlying carcinogenesis associated with the APC gene abnormality, it is necessary to determine the functions of the gene product, APC protein. APC protein, which is about 300 kDa in size, has been reported to bind with β-catenin, glycogen synthase kinase-3β (GSK-3β), as well as DLG in cells (Rubinfeld et al., Science, 262, 1731 (1993); Su et al., Science, 262, 1734 (1993); Rubinfeld et al., Science, 272, 1023 (1996); Matsumine et al., Science, 272, 1020 (1996)). Regarding functions of APC protein, it has been reported that the level of β-catenin is rapidly reduced when wild-type APC protein is expressed in colon cancer cell line SW480 having mutations in the APC gene (Munemitsu et al., Proc. Natl. Acad. Sci. USA, 92, 3046 (1995)). The central region containing a 7-repetitive structure is essential for the function of APC protein and coincides with a region where mutations are found in many colon cancer cases. It has also been reported that the β-catenin level is elevated in these colon cancer cells (Munemitsu et al., Proc. Natl. Acad. Sci. USA, 92, 3046 (1995); Rubinfeld et al., Cancer Res., 57, 4624 (1997)).

β-Catenin is also known as a membrane-skeletal protein for cell adhesion molecule cadherin and also reported to participate in the signal transduction of Wnt protein described below (Cadigan & Nusse, Genes Dev., 11, 3286 (1997)). Wnt gene is a large gene family of which members have a variety of functions in the processes of early embryogenesis and morphogenesis of animals; the family consists of about 20 types of genes in mouse and the genes are conserved among a variety of animals including African clawed frog (*Xenopus laevis*), fruit fly (*Drosophila melanogaster*), and nematoda (*Caenorhabditis elegans*). When Wnt protein binds to a receptor Frizzled, the activity of glycogen synthase kinase-3β (GSK-3β) is inhibited through an intracellular signaling molecule Dishvelled (Dsh). Since the phosphorylation of β-catenin mediated by GSK-3β causes the degradation of β-catenin, the inhibition of GSK-3β activity results in accumulation of β-catenin in cells. β-Catenin binds to a protein belonging to the transcription factor Lef/TCF family to form a complex and thereby activates the protein belonging to the Lef/TCF family as a transcription factor. Thus the accumulation of β-catenin results in formation of the β-catenin/TCF complex, which translocates to the nucleus and thereby stimulates the transcription of target genes. Among proteins belonging to the Lef/TCF family, TCf-4 is specifically expressed in the epithelium of colon, and thus it is believed that β-catenin chiefly forms a complex with TCf-4 in colon cancer (Korinek et al., Science, 275, 1784 (1997)). In addition, it has been reported that there are some colon cancer cells and melanoma cells where the APC gene is wild-type but the β-catenin gene has mutation and is not regulated by GSK-3β (Morin et al., Science, 275, 1787 (1997); Rubinfeld et al., Science, 275, 1790 (1997)). It has been estimated that, in these cells, β-catenin constantly accumulates, which results in transcriptional activation by the β-catenin/TCF complex.

Based on the above-described findings, β-catenin can be greatly involved in the onset of colon cancer. Therefore a substance capable of inhibiting the function of β-catenin through binding thereto can be associated with the onset of colon cancer and thus is predicted to be useful for the treatment, diagnosis, and such thereof. A protein molecule capable of binding to β-catenin, which was recently found, is Axin that negatively regulates the signal transduction of Wnt (Zeng et al., Cell, 90, 181 (1997)). Axin binds to GSK-3β and thereby stimulating the phosphorylation of β-catenin (Ikeda et al., EMBO J., 17, 1371 (1998)). Further it has been reported that Axin also binds to APC and β-catenin to stimulate the degradation of β-catenin and thereby lowering the level of β-catenin in cells (Kishida et al., J. Biol. Chem., 273, 10823 (1998); Rubinfeld et al., Current Biology, 8, 573 (1998); Nakamura et al., Genes to Cells, 3, 395 (1998)). However, there is no known proteins that binds to β-catenin and directly influences the activity of the β-catenin/TCF complex as a transcription factor.

DISCLOSURE OF THE INVENTION

An object of the present invention is to provide a protein capable of regulating transcriptional activation by β-catenin/TCF complex through binding to β-catenin, a DNA encoding the protein, an antibody recognizing the protein, a therapeutic agent containing the protein or the DNA, and a diagnostic agent containing the antibody, all of which are useful to treat and diagnose cancer.

The present invention relates to the following items (1) to (21):

(1) a protein having activities to bind to β-catenin and to inhibit transcriptional activation induced by formation of a complex of β-catenin with a protein belonging to the TCF/Lef family;

(2) The protein of (1), wherein the protein comprises the amino acid sequence of SEQ ID NO: 2 or 4;

(3) a protein comprising the amino acid sequence of SEQ ID NO: 2 or 4 in which one or more amino acids added, deleted, or substituted, and having activities to bind to δ-catenin and to inhibit transcriptional activation induced by formation of a complex of β-catenin with a protein belonging to the TCF/Lef family.

The above-mentioned amino-acid deletions, substitutions, or additions can be achieved by introducing site-directed mutations into a DNA encoding a protein comprising the amino acid sequence of SEQ ID NO: 2 or 4 by site-directed mutagenesis as described in Nucleic Acids Research, 10, 6487 (1982); Proc. Natl. Acad. Sci., USA, 79, 6409 (1982); Gene, 34, 315 (1985); Nucleic Acids Research, 13, 4431 (1985); Proc. Natl. Acad. Sci USA, 82, 488 (1985), etc.

(4) A DNA encoding the protein of any one of (1) to (3);

(5) a DNA comprising a nucleotide sequence selected from the group consisting of the nucleotide sequences of SEQ ID NOs: 1, 3, 5, and 6;

(6) a DNA that hybridizes to the DNA of (4) or (5) under stringent conditions, and that encodes a protein having activities to bind to β-catenin and to inhibit transcriptional activation induced by formation of a complex of β-catenin with a protein belonging to the TCF/Lef family.

The above-mentioned "DNA that hybridizes under stringent conditions, and that encodes a protein having activities to bind to β-catenin and to inhibit transcriptional activation induced by formation of a complex of β-catenin with a protein belonging to the TCF/Lef family" refers to a DNA that can be obtained by colony hybridization, plaque hybridization, Southern blot hybridization, or the like using a DNA having the nucleotide sequence of SEQ ID NO: 1 or 3 as a probe. Specifically, such DNA includes a DNA that can be identified by carrying out hybridization at 65° C. in the presence of 0.7 to 1.0 mol/L NaCl by using a filter, on which a DNA derived from a colony or plaque is immobilized, and then washing the filter under a condition of 65° C. with 0.1× to 2×SSC (saline-sodium citrate) solution [1×SSC solution (150 mmol/L NaCl, 15 mmol/L sodium citrate); nX means n times higher concentration of solution]. The hybridization can be performed according to a method as described in any of experimental manuals such as J. Sambrook et al., "Molecular Cloning, A Laboratory Manual, Second Edition," Cold Spring Harbor Laboratory Press (1989); F. M. Frederick et al., "Current Protocols in Molecular Biology, Supplement 1–38," John Wiley & Sons (1987–1997); D. M. Glover and B. D. Hames "DNA Cloning 1: Core Techniques, A Practical Approach, Second Edition," Oxford University Press (1995).

Specific examples of the DNA capable of hybridizing include a DNA exhibiting at least 80% or higher homology, preferably a DNA having 95% or higher homology to the nucleotide sequence of SEQ ID NO: 1 or 3, when the homology is computed by BLAST (J. Mol. Biol., 215, 403 (1990)), FASTA (Methods in Enzymology, 183, 63 (1990)), or the like.

(7) A recombinant DNA that can be obtained by inserting the DNA of any one of (4) to (6) into a vector;

(8) a transformant containing the recombinant DNA of (7);

(9) a method for producing the protein of any one of (1) to (3), wherein the method comprises the steps of culturing the transformant of (8) in a culture medium, producing and accumulating the protein of any one of (1) to (3) in a culture, and recovering the protein from the culture;

(10) a therapeutic agent for cancer, wherein the therapeutic agent comprises as an active ingredient the protein of any one of (1) to (3);

(11) a therapeutic agent for cancer, wherein the therapeutic agent comprises as an active ingredient the DNA of any one of (4) to (6);

(12) a vector for gene therapy for cancer, wherein the vector comprises the DNA of any one of (4) to (6);

(13) an oligonucleotide comprising a nucleotide sequence consisting of consecutive 5 to 60 residues from a nucleotide sequence of the DNA of any one of (4) to (6), an oligonucleotide comprising a sequence complementary to that of the oligonucleotide, or an oligonucleotide analogue which is derived therefrom;

(14) a diagnostic agent for cancer, wherein the diagnostic agent comprises as an active ingredient the oligonucleotide of (13);

(15) an antibody recognizing the protein of any one of (1) to (3);

(16) a method for immunologically detecting the protein of any one of (1) to (3), wherein the method utilizes the antibody of (15);

(17) a method for immunologically quantifying the protein of any one of (1) to (3), wherein the method utilizes the antibody of (15);

(18) a diagnostic agent for cancer, wherein the diagnostic agent comprises as an active ingredient the antibody of (15);

(19) the therapeutic agent of (10) or (11), wherein the cancer is colon cancer;

(20) the vector of (12), wherein the cancer is colon cancer; and

(21) the diagnostic agent of (18), wherein the cancer is colon cancer.

The present invention is described below in detail. In the following description, the protein of the present invention, having activities to bind to β-catenin and to inhibit transcriptional activation induced by formation of a complex of β-catenin with a protein belonging to the TCF/Lef family, is called an "inhibitor of β-catenin and TCF (hereafter abbreviated as ICAT)". Further, a DNA encoding ICAT is abbreviated as ICAT DNA.

1. Preparation of ICAT DNA

ICAT DNA can be obtained from cDNA encoding ICAT (hereafter abbreviated as ICAT cDNA) by the yeast two-hybrid system (S. Fields et al., Nature, 340, 245 (1989)). In other words, ICAT cDNA typically contains the untranslated regions, but ICAT DNA of the present invention contains only its coding region. The coding region can be determined as a region of open reading frame (ORF) (region covering the initiation codon to the termination codon in frame) by analyzing the nucleotide sequence of ICAT cDNA.

The yeast two-hybrid system is a method for detecting the binding between a protein of interest X (which is generally called "bait" in this method) and a protein Y, in which the detection is achieved by utilizing yeast transcription factor Z, such as GAL4, having a DNA-binding domain (BD) and a transcriptional activation domain (AD) in separate regions of the protein. Prepared at the first step are a plasmid (bait plasmid) for the expression of fusion protein between X and the DNA-binding domain of transcription factor Z (hereafter referred to as BD-X) in host yeast cells and another plasmid for the expression of fusion protein between Y and the transcription activation domain of transcription factor Z (hereafter referred to as AD-Y) in host yeast cells. Both plasmids are introduced into host yeast cells to co-express BD-X and AD-Y. The host yeast to be used is an yeast that can express a reporter gene under the regulation of a promoter where the transcriptional activation is achieved by the binding of transcription factor Z thereto. When protein Y has the ability to bind to protein X, then BD-X can bind to AD-Y. Because the resulting complex has the transcription factor Z-derived DNA-binding domain (BD) and transcriptional activation domain (AD), the complex, like transcription factor Z, results in the expression of the reporter gene. Accordingly, the binding between proteins X and Y can be detected by using the expression of the reporter gene as a marker. When, in this situation, instead of the AD-Y expression plasmid, a cDNA library where each cDNA can be expressed as a fusion protein with the transcriptional activation domain of Z are used without specifying Y, then transformants containing the cDNA encoding protein Y capable of binding to X can be isolated by the screening of the transformants based on the expression of reporter gene. Further, cDNAs of interest can be cloned by isolating the plasmids from the transformants.

A procedure for the cloning of ICAT cDNA by using the above-mentioned method is described below, where bait X is an armadillo domain of mouse β-catenin (hereafter abbreviated as mβ-catenin arm) as well as transcription factor Z is yeast GAL4.

(1) Preparation of Bait Plasmid

In the present invention, mβ-catenin arm (which corresponds to the amino acid sequence 141 to 664 of mouse β-catenin) was used as the bait. To prepare the bait plasmid, it is necessary to obtain a DNA encoding mβ-catenin arm (hereafter abbreviated as mβ-catenin arm DNA) to be used as the bait. Since the entire nucleotide sequence of mouse β-catenin DNA and the coding region of mouse β-catenin therein are known to those skilled in the art (GenBank accession No: M90364; Science, 257, 1142 (1992)), the nucleotide sequence corresponding to mβ-catenin arm DNA can readily be recognized. Accordingly, an mβ-catenin arm DNA can be amplified and isolated by the RT-PCR method shown below (M. J. McPherson et al., "PCR, A practical Approach," Oxford University Press (1991)).

Specifically, RNA is isolated from a mouse tissue or cells expressing β-catenin; cDNA is synthesized from the RNA; PCR is performed by using the cDNA as a template as well as using a sense primer corresponding to the 5' end of the nucleotide sequence of mβ-catenin arm DNA and an antisense primer containing a nucleotide sequence complementary to the 3' end of the nucleotide sequence. When the 5' end of each primer is designed to have a sequence of a restriction-enzyme recognition site of a cloning vector for bait plasmid as described below, then the amplified fragment can efficiently be inserted into the cloning vector for bait plasmid as described below by utilizing the restriction enzyme sites. If the primers are intended to have the restriction-enzyme recognition sequences for cloning, the primers are designed such that codons of the transcriptional activation domain of the transcription factor are in frame with those of mβ-catenin arm when inserted into the cloning vector.

The vector (to be preferably used to insert the mβ-catenin arm DNA prepared by the above-mentioned method) includes a vector capable of replicating in yeast *Saccharomyces cerevisiae*, and which has an appropriate marker gene for transformation, e.g., genes for amino acid biosynthesis such as TRP1 and LEU2, and can express the DNA-binding domain of GAL4 (hereafter abbreviated as GAL4 BD) under the regulation of a promoter for expression in yeast, e.g., alcohol dehydrogenase (ADH) promoter. In such cases, it is preferable to use a vector having appropriate restriction enzyme sites at a C-terminal portion of GAL4 BD for the insertion of mβ-catenin arm DNA, and capable of replicating in *E. coli* because of convenience to handle, e.g., to purify the vector DNA, as well as having a detectable marker for transformation in *E. coli*, e.g., the ampicillin-resistance gene. Such a vector includes pGBT9 (Clontech), pAS1 (T. Durfee et al., Genes & Development, 7, 555 (1993)), pAS2-1 (Clontech), or the like.

The above-mentioned mβ-catenin arm DNA prepared is isolated and then inserted at a restriction enzyme site on the C-terminal side of GAL4 BD in the vector in frame of codon.

(2) Preparation of cDNA Library for the Expression of Fusion Protein with the Transcriptional Activation Domain In order to prepare a cDNA library for the expression of a fusion protein with transcriptional activation domain of GAL4, the vector to be used can preferably replicate in yeast *Saccharomyces cerevisiae*, and which has an appropriate marker gene for transformation, e.g., genes for amino acid biosynthesis in yeast, such as TRP1 and LEU2, and can express the transcriptional activation domain of GAL4 (hereafter abbreviated as GAL4 AD) under the regulation of a promoter for expression in yeast, e.g., alcohol dehydrogenase (ADH) promoter. In such cases, it is preferable to use a vector having appropriate restriction enzyme sites at a C-terminal portion of GAL4 AD, and capable of replicating also in *E. coli* because of convenience to handle, e.g., to purify the vector DNA, as well as having a detectable marker for transformation in *E. coli*, e.g., the ampicillin-resistance gene. Such a vector includes pGAD (C. T.-Chien et al., Proc. Natl. Acad. Sci. USA, 88, 9578 (1991)), pGAD424 (Clontech), pACT (T. Durfee et al., Genes & Development, 7, 555 (1993)), pACT2-1 (Clontech), or the like.

Proteins capable of interacting with β-catenin in cells are predicted to be expressed in the same cells and tissues as β-catenin a is expressed. Accordingly, it is possible to prepare cDNA library by preparing cDNA from mouse tissues and cells where β-catenin is predicted to be expressed and inserting it at a restriction enzyme site on the C-terminal side of GAL4 AD in the above-mentioned vector for the expression of fusion protein. In such cases, when the orientations of the cDNA and GAL4 AD are same as each other and the two are in frame, then the fusion protein between GAL4 AD and the protein encoded by the cDNA can be expressed. Alternatively, it is possible to use a commercially available library usable in the yeast two-hybrid system, e.g., MATCHMAKER cDNA library (Clontech).

(3) Screening of cDNA by Yeast Two-Hybrid System

An yeast to be used for the introduction of the bait plasmid prepared in (1) and the cDNA library prepared in (2) includes yeasts belonging to *Saccharomyces cerevisiae*, into which the above-mentioned bait plasmid and cDNA library can be introduced, and further, it is required: (a) that the maker gene for transformation in the plasmid to be introduced and the gene in the host corresponding to the gene for transcription factor GAL4 used in the two-hybrid system are incapable of being expressed because of deletions or mutations thereof; and (b) that a nucleotide sequence to which GAL4 BD can bind has been inserted in the promoter region of an appropriate reporter gene. In this case, it is preferable to use a reporter gene of which transcription is readily detected when initiated by the binding with the bait, for example, genes for amino acid biosynthesis, e.g., HIS3, etc. (in this case, the gene should be different from that used as the maker for transformation of the bait plasmid), the *E. coli* β-galactosidase gene lacZ that is detectable in yeast, or the like. For example, the host yeast includes *Saccharomyces cerevisiae* CG1945 strain (Clontech), Y153 strain (Genes & Development, 7, 555 (1993)), CGY1::171 strain (Cell, 51, 121 (1987)), HF7C strain (Clontech), and others.

The bait plasmid prepared in (1) and the cDNA library prepared in (2) can be introduced into this host yeast to select transformants containing the cDNA encoding a protein capable of binding to mβ-catenin arm by using the expression of reporter gene as a marker. For example, colonies grown on a minimum medium without histidine are selected when the HIS3 gene for histidine biosynthesis is used as the reporter gene, or colonies expressing blue color in the presence of X-gal is selected when the *E. coli* lacZ gene is used as the reporter gene.

Since selected colonies of transformant contain both types of plasmids, the bait plasmid and cDNA library, only the plasmid of cDNA library is isolated according to the method as described in references ("DNA Cloning 2, Expression Systems, A Practical Approach, Second Edition," Oxford University Press (1995); Proc. Natl. Acad. Sci., 88, 9578 (1991)). Specifically, the isolation of the plasmid from the colony is followed by the transformation of *E. coli* therewith. In this case, the host *E. coli* to be used is a strain that does not express the marker gene contained in the cDNA library, so that the expression of the gene can be detected in the transformed strain. Some transformants expressing the marker gene contained in the cDNA library are selected from the transformants, and plasmid DNAs are isolated from the selected transformants to obtain cDNA clones.

(4) Analysis of Nucleotide Sequence of cDNA Clone

Nucleotide sequences of the cDNA clones obtained in (3) can be determined, by using the intact cDNA clones or alternatively after fragments of cDNA moiety are cut out with appropriate restriction enzymes and subcloned into appropriate cloning vectors, e.g., pUC118 and such, by a commonly used method for analyzing nucleotide sequence, e.g., the dideoxy-sequencing method by Sanger et al., (Proc. Natl. Acad. Sci. USA, 74, 5463 (1977)) or DNA sequencer provided by Perkin Elmer, etc.

It is possible to evaluated that the resulting nucleotide sequence of cDNA is novel, by verifying that the sequence of cDNA does not exhibit significant homology to nucleotide sequences of known genes deposited in databases in the search of nucleotide sequence databases, such as GenBank, EMBL, and DDBJ, using a program for homology search, such as BLAST.

When the nucleotide sequence is novel, then, as described in (2), the cDNA clone obtained in (3) should encode a fusion protein in which ICAT is connected to the C-terminus of GAL4 AD in frame. Accordingly, an ICAT amino acid sequence encoded by the cDNA can be deduced by translating the revealed nucleotide sequence of cDNA to a corresponding amino acid sequence in the same frame as the translational frame of GAL4 AD down to the stop codon in it.

Further, known genes exhibiting homology to the protein encoded by the cDNA can be selected by searching amino acid sequence databases, such as Genpept, PIR, and Swiss-Prot, for this amino acid sequence, with a program for homology search, such as BLAST, FASTA, and FrameSearch.

However, the resulting cDNA obtained may contain only a part downstream of the initiation codon of the full-length ICAT cDNA because, as described below in Example 11, ICAT can bind to mβ-catenin arm even when having a deletion of N-terminal 12 amino acids. In such cases, the ORF region is determined by using the same frame as the amino acids of ICAT obtained to reveal the entire amino acid sequence of ICAT, after a full-length ICAT cDNA is obtained by the method as described below in (5); the ORF region can be used as an ICAT DNA. In addition, as far as they encode the entire amino acid sequence of ICAT, the nucleotide sequences of the respective codons in ICAT DNA are not restricted to be identical those of the codons in the cDNA and it is possible to use any nucleotide sequences of codons that encode the same amino acid.

The novel cDNAs obtained as described above include, for example, cDNAs encoding proteins comprising amino acid sequences of SEQ ID NOs: 2 and 4.

(5) Cloning of Full-Length cDNA

When it is predicted that the length of ICAT cDNA obtained in (3) is not full length based on nucleotide sequence analysis in (4) as well as information on the length of mRNA obtained by Northern blot hybridization as described below, the full-length ICAT cDNA can be prepared by the following method.

(5-1) Screening of cDNA Library

The cDNA library prepared in (2) which expresses the fusion protein, or a cDNA library prepared from tissues or cells expressing β-catenin where ICAT is presumed to be co-expressed or cells where β-catenin mRNA is detected by Northern blotting as described below, and such, is screened by colony hybridization or plaque hybridization using as a probe the whole cDNA obtained in (3) or a part thereof, and then cDNA clones with the length that are presumed to be full-length are selected among the positive clones. The preparation and hybridization of cDNA library can be performed by the methods as described by J. Sambrook et al., "Molecular Cloning, A Laboratory Manual, Second Edition," Cold Spring Harbor Laboratory Press (1989) or others. Alternatively, it is possible to use commercially available cDNA libraries from Clontech or others. It is possible to reveal the entire nucleotide sequence of mouse ICAT cDNA by determining the nucleotide sequence of the resulting cDNA clones by the same method as described in (4) and also to reveal the entire amino acid sequence of mouse ICAT.

(5-2) RACE

Complementary DNAs are prepared from tissues or cells that are predicted to express ICAT, and then an adapter oligonucleotide is added to both ends of the cDNAs. Complementary DNA fragments containing a part extended to the 5' or 3' direction from the cDNA obtained in (3) can be obtained by 5'-RACE or 3'-RACE (Proc. Natl. Acad. Sci. USA, 85, 8998 (1988)) where PCR is carried out by using a primer from the nucleotide sequence of this adapter and a primer designed based on the nucleotide sequence of the cDNA clone obtained in (3).

The full-length ICAT cDNA can also be provided by determining nucleotide sequences of the resulting cDNAs in the same manner as in (4), and then connecting the obtained cDNAs and the cDNA clone obtained in (3) to each other, based on the nucleotide sequences determined.

(5-3) Use of EST Nucleotide Sequence

When the nucleotide sequence of ICAT cDNA determined in (4) is analyzed by searching public nucleotide sequence databases for homology, identical sequences to that of the cDNA may be found among partial sequences of random cDNA clones, ESTs, even when there is no identical nucleotide sequence among known genes. In such cases, these ESTs and other ESTs containing nucleotide sequences identical to that of the ESTs and ESTs derived from the same clone are all collected together as the ESTs derived from the same gene. Sometimes a longer nucleotide sequence extended in the 5' or 3' direction as compared with the cDNA obtained in (3) may be found by assembling the nucleotide sequences of these ESTs presumed to be derived from ICAT cDNA. In such cases, it is possible to obtain an extended portion of cDNA located on the 5' or 3' side of the cDNA nucleotide sequence obtained in (4) by RT-PCR using a sense primer having the nucleotide sequence of 5' end of the nucleotide sequence obtained from the assembled ESTs or an antisense primer having an nucleotide sequence complementary to the nucleotide sequence of the 3' end thereof. Complementary DNA or cDNA library derived from mouse tissues or cells which are predicted to express ICAT can be used as a template in the RT-PCR. Nucleotide sequence of the obtained cDNA is determined in the same manner as described in (4). When many ESTs that are presumed to be derived from mouse ICAT cDNA are obtained in public nucleotide sequence databases, the full-length cDNA nucleotide sequence of mouse ICAT may be revealed, without RT-PCR, by assembling the collected EST nucleotide sequences.

Further, once the full-length nucleotide sequence of ICAT cDNA has revealed as described above, ICAT cDNA can be obtained by PCR using as a template cDNA or cDNA library prepared from mouse tissues or cells, which is predicted to express ICAT, in the same manner as described in (3) as well as primers designed based on the nucleotide sequence of the cDNA. A transformant containing the resulting mouse ICAT cDNA clone pmICAT, *Escherichia coli* DH5α/pmICAT, has been deposited under an accession number FERM BP-6701 in the National Institute of Bioscience and Human-Technology, National Institute of Advanced Industrial Science and Technology (1-1-3 Higashi, Tsukuba, Ibaraki, Japan 305-8566) as of Apr. 14, 1999.

In addition, ICAT DNA can be synthesized chemically in a DNA synthesizer based on the nucleotide sequence of ICAT cDNA determined as described above. Such a DNA synthesizer includes DNA synthesizer model 392 from Perkin Elmer utilizing phosphoramidite method, and the like.

(6) Isolation of DNA Encoding Human ICAT

It is more important to obtain human ICAT or the encoding DNA (hereafter abbreviated as human ICAT DNA) than the mouse ICAT to analyze the mechanism underlying the onset of human colon cancer as well as to treat and diagnose the cancer. In general, proteins from different species having the same function often have amino acid sequences not identical but exhibiting homology to each other. Accordingly, the DNAs encoding the proteins are also predicted to exhibit homology to each other. In addition, mutations are accumulating in genes during the evolution of organisms, and therefore it can be assumed that the closer the lineage of the species phylogenetically, the higher the homology. Accordingly, it is possible to obtain ICAT DNA from other mammal, for example, human ICAT DNA, by utilizing the nucleotide sequence of mouse ICAT DNA obtained in (3) according to a method as described below. Without obtaining mouse ICAT DNA, human ICAT DNA can be obtained directly through the same procedures as described in (1) to (5) of yeast two-hybrid system with bait plasmid in which armadillo domain of human β-catenin (J. Cell Biol., 127, 2601 (1994)) is used as the bait and human cDNA library.

(6-1) Screening of cDNA Library

Because human ICAT can be assumed to have the same function as mouse ICAT, human ICAT is predicted to be expressed in the same tissues and cells as mouse ICAT. Accordingly, it is possible to obtain cDNA clones for human ICAT from a cDNA library such as cDNA library prepared from a human tissue equivalent to mouse tissue where mouse ICAT is expressed or cells derived from such human tissues according to the same method as described in (5-1), or alternatively from a commercially available human cDNA library derived from such a human tissue or cells, by carrying out colony hybridization or plaque hybridization using mouse ICAT DNA labeled with radioisotope, digoxigenin, or the like as a probe.

(6-2) Use of EST

Public nucleotide sequence databases such as GenBank are searched by using a program of homology search to find human ESTs exhibiting homology to the nucleotide sequence of mouse ICAT DNA obtained in (4). Since such ESTs exhibiting homology to a mouse ICAT DNA, is presumed to be derived from human ICAT cDNA, at least a part of nucleotide sequence of human ICAT cDNA can be obtained by assembling the nucleotide sequences of the ESTs. Among clones that were used to determine the nucleotide sequences of the ESTs, clones from Integrated Molecular Analysis of Genome Expression Consortium (I.M.A.G.E. Consortium) as well as from The Institute for Genomic Research (TIGR) are distributed from ATCC. Also, it is possible to obtain a cDNA clone covering the entire human ICAT cDNA by assembling cDNAs clones obtained, which can be presumed to contain the 5' end, 3' end, or a central part of human ICAT cDNA based on the nucleotide sequences of ESTs. A transformant containing the resulting full-length human ICAT cDNA clone phICAT, *Escherichia coli* DH5α/phICAT, has been deposited under an accession number FERMBP-6700 in the National Institute of Bioscience and Human-Technology, National Institute of Advanced Industrial Science and Technology (1-1-3 Higashi, Tsukuba, Ibaraki, Japan 305-8566) as of Apr. 14, 1999.

It is also possible to obtain human ICAT cDNA by the amplification with RT-PCR in the same manner as described in (3) using primers prepared as to correspond to the 3' end and 5' end of the nucleotide sequence of human ICAT cDNA nucleotide sequence as well as using, as a template, RNA prepared from human tissues or cells which are predicted to express ICAT.

The human ICAT DNA is determined as an ORF region from the full-length human ICAT cDNA obtained according to the procedure as described above. Even if there are a number of ORFs, an ORF that has homology to the definite ORF in the mouse ICAT cDNA can be selected as the human ICAT DNA because mouse ICAT and human ICAT are assumed to have homology in amino acid sequence. The amino acid sequence of human ICAT can be determined as an amino acid sequence encoded by the ORF.

(7) Preparation of ICAT Oligonucleotide

It is possible to prepare an oligonucleotide containing a partial sequence of ICAT DNA in accordance with the present invention or an oligonucleotide having a nucleotide sequence complementary thereto (hereafter abbreviated as ICAT oligonucleotide) in the DNA synthesizer described in (5).

Specifically, the ICAT oligonucleotide includes a DNA having the same sequence as consecutive 5 to 60 nucleotides in the nucleotide sequence of SEQ ID NO: 1 or 3, or DNA having a sequence complementary to the DNA. When used as a sense primer or antisense primer, these DNAs are preferably oligonucleotides of which melting temperatures and the numbers of nucleotides are not considerably deviated from others.

Any analogues of the oligonucleotides (hereafter also referred to as oligonucleotide analogues) are included by the oligonucleotide of the present invention. The oligonucleotide analogues are exemplified by oligonucleotide derivatives in which the phosphodiester bond of the oligonucleotide has been converted to a phosphorothioate bond; oligonucleotide analogues in which phosphodiester bond in the oligonucleotide has been converted to a N3'—P5' phosphoramidate bond; oligonucleotide analogues in which the phosphodiester bond between the ribose and phosphate in the oligonucleotide has been converted to a peptide-nucleic acid bond; oligonucleotide analogues in which uracil in the oligonucleotide has been the substituted with C-5 propynyluracil; oligonucleotide analogues in which uracil in the oligonucleotide has been substituted with C-5 thiazoleuracil; oligonucleotide analogues in which cytosine in the oligonucleotide has been substituted with C-5 propynylcytosine; oligonucleotide analogues in which cytosine in the oligonucleotide has been substituted with phenoxazine-modified cytosine; oligonucleotide analogues in which the ribose in the oligonucleotide has been substituted with 2'-O-propyl-ribose; oligonucleotide analogues in which the ribose in the oligonucleotide has been ribose substituted with 2'-methoxyethoxyribose, and such (Cell Technology, 16, 1463 (1997)).

2. Production of ICAT

ICAT of the present invention can be produced by expressing ICAT DNA as prepared in Section 1 in host cells according to a method as described in "Molecular Cloning, A Laboratory Manual, Second Edition" (J. Sambrook et al., Cold Spring Harbor Laboratory Press (1989)), "DNA Cloning 1: Core Techniques, A Practical Approach, Second Edition" (D. M. Glover and B. D. Hames, Oxford University Press (1995)), etc.

Specifically, ICAT of the present invention can be produced by preparing a recombinant vector in which ICAT DNA has been inserted downstream of a promoter in an appropriate expression vector, introducing the vector in host cells to obtain a transformant expressing ICAT, and then culturing the transformant.

The expression vector to be used is a vector that is capable of autonomous replication or being integrated into chromosome in host cells and contains a promoter directing transcription from ICAT DNA to mRNA in host cells.

Any host cells can be used including prokaryotic cells, yeast cells, animal cells, insect cells, plant cells, and so on, as far as the cells can express the gene of interest. Animal individuals and plant bodies are also usable.

When prokaryotes such as bacteria are used as host cells, then ICAT expression vector to be used is capable of autonomous replication in the host prokaryote and in which ICAT DNA has been placed downstream of a promoter containing ribosome-binding sequence. It is preferable that the distance between the ribosome-binding sequence and the initiation codon has been adjusted appropriately (for example, 6 to 18 nucleotides for a vector of *E. coli* host). It is preferable to place a transcription termination sequence immediately downstream of ICAT DNA, although it is not essential in the invention. In addition, the vector should be designed to contain sequences for the expression of marker gene such as drug-resistance genes for the convenience of selection of transformants.

Any promoter can be used, as far as it has the ability to direct the expression in host cells. For example, when *E. coli* is used as a host, the promoters include promoters derived from *E. coli* and phage, such as trp promoter (Ptrp), lac promoter (Plac), $P_L$ promoter, T7 promoter, $P_R$ promoter, etc. It is also possible to use artificially designed or modified promoters, such as a promoter in which two Ptrp are connected to each other tandemly, tac promoter, T7-lac promoter, let I promoter, etc. When *Bacillus subtilis* is used as a host, the promoters include promoters derived from SPO1 and SPO2 that are *Bacillus subtilis* phages as well as PenP promoter.

The expression vector is exemplified, for example, by pSE280 (Invitrogen), pGEMEX-1 (Promega), pQE-8 (QIAGEN), pKYP200 (Agric. Biol. Chem., 48, 669 (1984)), pLSA1 (Agric. Biol. Chem., 53, 277 (1989)), pGEL1 (Proc. Natl. Acad. Sci., USA, 82, 4306 (1985)), pBluescript II SK(−) (Stratagene), pKK223-3 (Amersham Pharmacia 1>Biotech), pGEX-5X-3 (Amersham Pharmacia Biotech), and pET14 (Novagen).

The host cells can be microorganisms belonging to the genus *Escherichia*, the genus *Serratia*, the genus *Bacillus*, the genus *Brevibacterium*, the genus *Corynebacterium*, the genus *Microbacterium*, w the genus *Pseudomonas*, and so on, for example, *Escherichia coli* XL1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49, *Serratia ficaria, Serratia fonticola, Serratia liquefaciens, Serratia marcescens, Bacillus subtilis, Bacillus amyloliquefaciens, Brevibacterium ammoniagenes, Brevibacterium immariophilum* ATCC14068, *Brevibacterium saccharolyticum* ATCC14066, *Corynebacterium glutamicum* ATCC13032, *Corynebacterium glutamicum* ATCC14067, *Corynebacterium glutamicum* ATCC13869, *Corynebacterium acetoacidophilum* ATCC13870, *Microbacterium ammoniaphilum* ATCC15354, *Pseudomonas* sp. D-0110.

Any method for introducing recombinant vectors can be used, as far as such a method has the ability to introduce DNAs to the above-mentioned host cells. Such methods include, for example, electroporation (Nucleic Acids Res., 16, 6127 (1988)), methods using calcium ion (Proc. Natl. Acad. Sci. USA, 69, 2110 (1972)), protoplast method (Japanese Published Unexamined Patent Application 248394/88), or other methods as described in Gene, 17, 107 (1982) or Molecular & General Genetics, 168, 111 (1979).

When yeast is used as a host cell, expression vectors to be utilized include vectors containing a promoter capable of directing the transcription in host yeast, ICAT DNA, transcription termination sequence, and a sequence capable of the expression of a maker gene for transformation in yeast (e.g., drug resistance genes and genes for amino acid biosynthesis such as TRP1, HIS3, and LEU2). Further, it is preferable to use an expression vector capable of autonomous replication and capable of expressing a drug-resistance gene that can be utilized as a marker for transformation in *E. coli* for the convenience of preparation and maintenance of the vector.

Any promoter can be used, as far as it has the ability to direct the transcription in yeast. Such promoters include, for example, promoters of the alcohol dehydrogenase gene ADH1 and genes involved in galactose metabolism, e.g., GAL1, GAL10, and such, promoter of the acid phosphatase gene PHO5, promoter of the phosphoglycerate kinase gene PGK, promoter of the glycelaldehyde-3-phosphate dehydrogenase gene GAP, promoters of genes for heat shock proteins, promoter of α-mating factor gene MFα1, and promoter of the copper-metallothionein gene CUP1 derived from *Saccharomyces cerevisiae* as well as promoter of alcohol oxidase gene AOX1 derived from *Pichiapastoris*.

The host cells include yeast strains belonging to the genus *Saccharomyces*, the genus *Schizosaccharomyces*, the genus *Pichia*, the genus *Candida*, and so on, specifically, include *Saccharomyces cerevisiae, Schizosaccharomyces pombe, Pichia pastoris, Candida utilis*, etc.

Any method for introducing recombinant vectors can be used, as far as such a method has the ability to introduce DNAs to yeast. Such methods include, for example, electroporation (Methods. Enzymol., 194, 182 (1990)), spheroplast method (Proc. Natl. Acad. Sci. USA, 81, 4889 (1984)), lithium acetate method (Journal of Bacteriology, 153, 163 (1983)), etc.

When animal cells are used as hosts, expression vectors to be utilized include vectors containing a promoter capable of directing the transcription in host animal cells, ICAT DNA, and signal sequences for transcription termination and polyadenylation of the transcripts. Further, it is preferable to use an expression vector capable of autonomous replication and capable of expressing a drug-resistance gene that can be utilized as a marker for transformation in *E. coli* for the convenience of preparation and maintenance of the vector. Any promoter can be used, as far as it has the ability to direct the transcription in animal cells. Such promoters include virus-derived sequences, such as SV40 early promoter, promoter and enhancer elements of human cytomegalovirus IE (immediate early) gene, LTRs originating from retroviruses such as Rous sarcoma virus, human T cell leukemia virus I, Moloney murine leukemia virus, etc.; or promoters from genes, such as metallothionein gene, β-actin gene, elongation factor-1, and such, derived from animal cells. Further it is possible to use artificial promoters in which multiple promoter elements as listed above have been combined together, e.g., SRα promoter created by combining SV40 early promoter and LTR from human T cell leukemia virus I.

Cells in which ICAT DNA has been integrated in the host chromosomal DNA and which constitutively expresses ICAT can be selected by introducing an ICAT expression vector containing a sequence for the expression of a drug-resistance gene against a drug such as G418 or hygromycin into the host cells and culturing the cells in the presence of the drug. Further, in order to increase the amount of ICAT produced in host cells, a vector for the constitutive expression of ICAT, which contains a sequence for the expression of the dihydrofolate reductase (dhfr) gene, is introduced into host cells, and the cells are cultured while the concentration of methotrexate as a dhfr inhibitor is successively being increased; and thus it is possible to successfully achieve the amplification of the copy number of ICAT DNA together with that of the dhfr gene. Such host cells, in which the gene amplification utilizing the dhfr gene is achieved, can be cells that have no functional dhfr gene, for example, CHO/dhfr⁻ (ATCC: CRL-9096) or the like.

Vectors to be used for the preparation of the above-mentioned ICAT expression vector specifically include, for example, pAGE107 (Japanese Published Unexamined Patent Application 22979/91; Cytotechnology, 3, 133, (1990)), pAS3-3 (227075/90), pCDM8 (Nature, 329, 840 (1987)), pcDNA3.1(+) (Invitrogen), pREP4 (Invitrogen), pBK-RSV (Stratagene), pSVK3 (Amersham Pharmacia Biotech), pcDNA1.1/Amp (Invitrogen), pAMo (J. Biol. Chem., 268, 22782 (1993)), or the like.

The host cells include cell lines such as human-derived cells, HeLa and Namalwa as well as human kidney cell line 293 (ATCC: CRL-1573); COS-1 and COS-7 that are kidney cells form African green monkey; CHO and BHK cells from hamster; SP2/0 and NS0 cells of mouse myeloma, rat myeloma cell YB2/0.

Any method for introducing recombinant vectors can be used, as far as such a method has the ability to introduce DNAs to animal cells. Such methods include, for example, electroporation (Cytotechnology, 3, 133 (1990)), calcium-phosphate method (227075/90), lipofection method (Proc. Natl. Acad. Sci. USA, 84, 7413 (1987)), etc.

When insect cells are used as host cells, the baculovirus expression system (Baculovirus Expression Vectors, A Laboratory Manual, W.H. Freeman and Company, New York (1992), Bio/Technology, 6, 47 (1988)) can be utilized. Specifically, after ICAT DNA was inserted in a vector called transfer vector, both vector and baculovirus are concurrently introduced into insect cells; the resulting homologous recombination provides a recombinant baculovirus in which ICAT DNA has been inserted downstream of the polyhedrin gene promoter that is a highly efficient promoter; then, the recombinant baculovirus can be infected to the insect cells, and thereby achieving the expression of ICAT.

Such baculovirus to be utilized includes *Autographa californica* nuclear polyhedrosis virus, *Bombyx mori* nuclear polyhedrosis virus, etc. The insect cells to be used can be Sf9 and Sf21 that are cells derived from *Spodoptera frugiperda* (Baculovirus Expression Vectors, A Laboratory Manual, New York (1992)), High5 (Invitrogen) which is a cell derived from *Trichoplusia ni* or the like. Alternatively, silkworm larvae per se are also usable. The transfer vector contains the polyhedrin promoter and a sequence derived from baculovirus for directing homologous recombination, as well as sequences for the maintenance and replication of vector as well as for the insertion of foreign genes (a sequence capable of autonomous replication in *E. coli* and a sequence of drug resistance gene), and such for the convenience of gene manipulation in *E. coli*. Specifically such vectors include pVL1392, pVL1393, pBluebac4 (both from Invitrogen), etc.

ICAT can be produced by using animal individuals. For example, ICAT can be produced in an animal body in which ICAT DNA has been introduced according to a known method (American Journal of Clinical Nutrition, 63, 639S (1996); American Journal of Clinical Nutrition, 63, 627S (1996); Bio/Technology, 9, 830 (1991)).

Any promoter can be used, as far as it has the ability to direct the expression in animals. For example, it is possible to preferably use α-casein promoter, β-casein promoter, β-lactoglobulin promoter, whey acidic protein promoter, and so on that are promoters specific to mammary gland cells.

When plant cells or plant bodies are used as hosts, ICAT can be produced according to a known method (Tissue Culture, 20 (1994); Tissue Culture, 21 (1995); Trends in Biotechnology, 15, 45 (1997)).

Any promoter for the expression of ICAT DNA can be used, as far as it has the ability to direct the gene expression in plant cells. Such promoters include, for example, 35S promoter of cauliflower mosaic virus, actin-1 promoter of rice, etc. Further, intron 1 of the maize alcohol dehydrogenase gene and such can be inserted between the promoter and ICAT DNA to be expressed to increase the efficiency of expression of ICAT DNA.

The host cells can be plant cells derived from potato, tobacco, maize, rice, rape, soybeans, tomato, wheat, barley, rye, alfalfa, flax, etc.

Any method for introducing recombinant vectors can be used, as far as such a method has the ability to introduce DNAs to plant cells. Such methods include, for example, a method using *Agrobacterium*, electroporation (Cytotechnology, 3, 133 (1990)), method using particle gun (gene gun), etc.

Plant cells or organs in which ICAT DNA has been introduced can be cultured on a large scale by using jar fermenter. Also, plant cells containing introduced genes can be regenerated to create plant bodies (transgenic plant) in which ICAT DNA has been introduced.

Microorganisms, animal cells, or transformants derived from a plant cell, which contain a recombinant vector containing the ICAT DNA of the present invention as an insert, can be cultured according to a typical culture method, ICAT is allowed to accumulate in them, and ICAT is recovered from the culture, in order to produce ICAT.

Media to be used for the cultivation of transformants obtained by using animal cells as hosts include commonly used RPMI1640 medium (The Journal of the American Medical Association, 199, 519 (1967)) Eagle's MEM (Science, 122, 501 (1952)), DMEM (Virology, 8, 396 (1959)) 199 medium (Proceeding of the Society for the Biological Medicine, 73, 1 (1950)) and these media containing fetal calf serum or the like. If desired, an antibiotic such as penicillin or streptomycin may be added to the medium. Typically the cultivation can be performed under a condition such as at pH 6 to 8 at 30 to 40° C. in the presence of 5% $CO_2$ for 1 to 7 days.

Media to be used for the cultivation of transformants obtained by using insect cells as host cells include commonly used TNM-FH medium (Pharmingen), Sf-900 II SFM medium (Life-Technologies), ExCell400, ExCell405 (both from JRH Biosciences), Grace's Insect Medium (Nature, 195, 788 (1962)). In a preferable culture condition, pH is 6 to 7; culture temperature is 25 to 30° C., and culture typically is continued for 1 to 5 days. Further, if desired, an antibiotic such as gentamicin may be added to the medium during the culture.

When the transformant is an animal individual or a plant body, it is possible to produce ICAT by breeding or cultivating it according to a typical method, allowing ICAT to accumulate in it and recovering ICAT from the animal individual or plant body.

Specifically, in the case of an animal individual, for example, it is possible to produce ICAT by breeding a non-human transgenic animal containing ICAT DNA, allowing ICAT encoded by the recombinant DNA to be produced and accumulated in the animal body, and recovering ICAT from the animal. The site for the production and accumulation of ICAT in the animal include, for example, milk or egg of the animal.

In the case of plant body, for example, it is possible to produce ICAT by cultivating transgenic plant containing ICAT DNA, allowing ICAT encoded by the recombinant DNA to be produced and accumulated in the plant, and recovering ICAT from the plant.

Any of natural media and synthetic media can be used for the culture of transformant obtained by using as a host a prokaryote such as *E. coli* or eukaryote such as yeast, as far as it contains carbon source, nitrogen source, inorganic salts, and so on which the organism can assimilate and the culture of the transformant is achieved efficiently in it.

Any carbon source that is assimilated by the organisms can be used, including glucose, fructose, sucrose, and molasses containing them; carbohydrates such as starch and starch hydrolysate; organic acids such as acetic acid and propionic acid; alcohols such as ethanol and propanol.

Nitrogen source that can be utilized includes ammonia, ammonium chloride, inorganic acids such as ammonium sulfate, ammonium acetate, ammonium phosphate or ammonium salts of organic acid, other nitrogen-containing compound, as well as, peptone, meat extract, yeast extract, corn steep liquor, casein hydrolysate, soybean cake and soybean cake hydrolysate, various fermentation microorganisms, and the digests thereof.

Such inorganic substances include potassium dihydrogenphosphate, dipotassium hydrogenphosphate, magnesium phosphate, magnesium sulfate, sodium chloride, ferrous sulfate, manganese sulfate, copper sulfate, calcium carbonate, etc.

The culture is typically carried out under an aerobic condition such as by shaking culture or deep-aerobic culture with stirring. It is preferable to perform the culture at 15 to 40° C. and typically for 16 to 96 hours. The pH should be maintained to be 3.0 to 9.0 during the culture. The adjustment of pH can be conducted by using an inorganic or organic acid, alkaline solution, urea, calcium carbonate, ammonia, etc. If desired, an antibiotic such as ampicillin or tetracycline may be added to the medium during the culture.

In the case of culturing microorganisms transformed with an expression vector using an inducible promoter, if desired, an inducer can be added to the medium. For example, in the case of culturing microorganisms transformed with an expression vector using lac promoter, IPTG or the like can be added to the medium; and in the case of culturing microorganisms transformed with an expression vector using trp promoter, indoleacrylic acid or the like can be added to the medium.

The following typical methods for the isolation and purification of proteins can be used to isolate and purify ICAT accumulated in the culture of the above-mentioned transformant.

When ICAT is secreted from the cells, ICAT accumulates in the medium. Accordingly, after the culture is completed, medium alone, from which the cells have been removed, can be recovered by techniques such as centrifugal separation. It is possible to obtain purified sample from the medium by using typical methods singly or in combination for the isolation and purification of proteins; specifically, solvent extraction, salting out using ammonium sulfate or the like, desalting, organic-solvent precipitation, anion exchange chromatography using resins such as DEAE Sepharose, DIAION HPA-75 (Mitsubishi Chemical), Mono-Q (Amersham Pharmacia Biotech), and so on, cation exchange chromatography using resins such as SP Sepharose (Amersham Pharmacia Biotech), and such, hydrophobic chromatography using resins such as butyl-Sepharose, phenyl-Sepharose, gel filtration using molecular sieve, affinity-chromatography, chromato-focusing, electrophoretic techniques such as isoelectric focusing, etc.

When ICAT is accumulated in cells of transformant, after the culture is completed, the cells of transformant are recovered from the culture by a technique such as centrifugation, subsequently suspended in a buffer and then crushed by using a sonicator, French press, or the like to give cell-free extract. When ICAT is soluble in the cells, purified sample can be obtained from the supernatant after centrifuging the cell-free extract by the same method as used for the purification and isolation from the above-mentioned medium. Alternatively, when ICAT is present as inclusion bodies in cells, the cell-free extract is treated by centrifugation, and then the inclusion bodies of ICAT can be recovered as precipitated fraction. This inclusion bodies of ICAT is solubilized by a protein denaturant, and then the resulting solution is dialyzed as to contain no protein denaturant or so dialyzed or diluted that such a low level of protein denaturant does not denature the protein to restore the normal tertiary structure of ICAT. Subsequently, purified sample can be obtained by the same method for the isolation and purification as described above.

In addition, ICAT can be produced by in vitro transcription-translation system according to a known method of (J. Biomolecular NMR, 6, 129–134, Science, 242, 1162–1164, J. Biochem., 110, 166–168 (1991)). Specifically, ICAT DNA is ligated downstream of a promoter such as SP6, T7, or T3, an RNA polymerase specific to each promoter is allowed to react thereto for the synthesis of large amount of ICAT RNA in vitro, and then ICAT can be produced by a cell-free translation system, e.g., translation system utilizing rabbit reticulocyte lysate or wheat germ extract.

The structural analysis for the purified ICAT can be carried out by a commonly used method in protein chemistry, for example, a method as described in "Protein Structural Analysis for Gene Cloning" (H. Hirano, Tokyo Kagaku Doujin, 1993).

The presence of binding of ICAT or a derivative thereof, in which the amino acid sequence has substitutions, deletions, or additions, with the complex between β-catenin and a protein belonging to the TCF/Lef family can be determined by evaluating whether the transcription of the reporter gene is detected or not, by using an expression vector for a fusion protein between the transcriptional activation domain and each of the proteins encoded by the DNAs as well as by using a bait plasmid for β-catenin in the yeast two-hybrid system as shown in Section 1. Alternatively, ICAT or a derivative thereof is directly mixed with β-catenin in vitro and allowed to bind, or alternatively after ICAT or a derivative thereof is expressed in cells and allowed to bind in cells, immunoprecipitation is carried out for the reaction solution or the cell extract by using an antibody against β-catenin; then the presence of ICAT or a derivative thereof in the precipitate is evaluated by Western blotting or the like, and thereby achieving the determination of the presence of binding. Alternatively, instead of the use of the antibody, a fusion protein is prepared, which consists of ICAT or a derivative thereof and a protein or peptide such as GST for the convenience of purification, and the fusion protein is allowed to bind to β-catenin labeled with such as $^{35}$S; after the ICAT fusion protein is purified, the presence of labeled β-catenin in purified material is detected to determine the presence of binding.

Furthermore, it is possible to determine whether not only ICAT or a derivative thereof can bind to a complex between β-catenin and a protein belonging to the TCF/Lef family but also can inhibit the activity of the complex of activating the transcription, by using a plasmid in which a reporter gene, such as luciferase, chloramphenicol-acetyltransferase, or β-galactosidase, placed downstream of a promoter which contains a TCF binding sequence and such that the transcription is activated by a complex between β-catenin and a protein belonging to the TCF/Lef family, for example, pTOPFLASH and PTOPCAT (Science, 275, 1784 (1997)). The above-mentioned expression plasmid with a reporter gene is introduced, into animal cells together with an expression plasmid for a mutant β-catenin which can constantly bind to a protein belonging to the TCF/Lef family and thus can activate the transcription, for example, a mutant β-catenin in which serine residue 33 has been substituted with tyrosine; an expression plasmid of ICAT or a derivative thereof is further added thereto or not added, and then the level of reporter-gene expression is assayed and compared between the two cases, thereby to determine whether or not ICAT or a derivative thereof can inhibit the transcription activation.

3. Preparation of Antibody Recognizing ICAT (1) Preparation of Polyclonal Antibody Full-length ICAT or a partial fragment of the protein, which is obtained by the method as describe above in section 2, can be used as an antigen and administered into an animal to prepare a polyclonal antibody.

Such animals that can be utilized for the administration include rabbit, goat, rat, mouse, hamster, etc. It is preferable to use the antigen in an administration dose of 50 to 100 μg/animal.

When a peptide is used for this purpose, it is preferable to use the peptide as an antigen after covalently linked to a carrier protein such as KLH or bovine thyroglobulin.

After the first administration, the antigen is given 3 to 10 times at 1 to 2-week intervals. 3 to 7 days after each time of administration, blood is collected from the venous plexus of eyegrounds. Then the serum is tested for the reactivity to the antigen used for the immunization by using a method of enzyme immuno-assay ("Methods of Enzyme Immuno-Assay (ELISA): Igakushoin, 1976; "Antibodies: A Laboratory Manual," Cold Spring Harbor Laboratory Press (1988)), etc.

It is possible to obtain the polyclonal antibody by collecting the sera from non-human mammals that have exhibited sufficiently high antibody titers in their sera against the antigen used for the immunization, and separating and purifying the sera.

Such methods for the separation and purification include centrifugal separation, salting out with 40 to 50% saturated ammonium sulfate, precipitation by caprylic acid ("Antibodies: A Laboratory Manual," Cold Spring Harbor Laboratory, (1988)), and a procedure for processing using singly or in combination chromatographic methods, e.g., using DEAE-Sepharose column, anion exchange column, protein-A or -G column, gel filtration column, etc.

(2) Preparation of Monoclonal Antibody (2-1) Preparation of Antibody-Producing Cells Rats, of which sera have exhibited sufficiently high titers of antibody against the antigen used for the immunization as describe above in (1), are provided as the source of antibody-producing cells.

3 to 7 days after the final administration of the antigen substance to the rats which have exhibited such antibody titers, their spleens are removed from them.

The spleens are sectioned into small pieces in MEM and crushed by forceps. After centrifugation at 1200 rpm for 5 minutes, the supernatant is discarded.

The resulting precipitated fraction of spleen cells is treated with Tris-ammonium chloride buffer (pH 7.65) for 1 to 2 minutes to remove red blood cells then the spleen cells are washed 3 times with MEM. The spleen cells prepared are used as antibody-producing cells.

(2-2) Preparation of Myeloma Cells

Myeloma cell to be used is a cell line established from mouse or rat. For example, 8-azaguanine resistant mouse (BALB/c-derived) myeloma cell lines that are usable include P3-X63Ag8-U1 (P3-U1) (Curr. Topics Microbiol. Immunol., 81, 1 (1978); Eur. J. Immunol., 6, 511 (1976)), SP2/0-Ag14(SP-2) (Nature, 276, 269 (1978)), P3-X63-8653 (653) (J. Immunol., 123, 1548 (1979)), P3-X63-Ag(X63) (Nature, 256, 495 (1975)), and the like. Cells of these lines are passaged in 8-azaguanine medium [RPMI1640 medium containing 1.5 mmol/L glutamine, $5\times10^5$ mol/L 2-mercaptomethanol, 10 µg/ml gentamicin, and 10% fetal calf serum (CSL) (hereafter referred to as normal medium) further containing 15 µg/ml 8-azaguanine], but 3 to 4 days before the cell fusion the cells are cultured in the normal medium. $2\times10^7$ or more cells are used for the fusion.

(2-3) Preparation of Hybridoma

The antibody-producing cells prepared as described in (2-1) and myeloma cells in (2-2) are washed well with MEM or PBS (1.83 g of disodium phosphate, 0.21 g of potassium dihydrogenphosphate, 7.65 g of sodium chloride, 1 L of distilled water; pH 7.2), the cells are mixed with each other at a ratio of the numbers of antibody-producing cells: myeloma cells=5 to 10:1. After the mixture was subjected to centrifugation at 1200 rpm for 5 minutes, the supernatant is discarded.

The mixed cells prepared from the precipitated fraction are well dispersed. While the cells are being stirred at 37° C., 0.2 to 1 ml (per $10^8$ antibody-producing cells) of a solution of 2 g PEG-1000, 2 ml MEM, and 0.7 ml DMSO is added to the cell mixture; then 1 to 2 ml of MEM is added thereto several times at 1 to 2-minute intervals.

After the addition, the cells are so prepared by further adding MEM that the total volume becomes 50 ml.

The suspension prepared is subjected to centrifugation at 900 rpm for 5 minutes, and then the supernatant is discarded.

The cells from the resulting precipitated fraction are gently dispersed and then suspended by gentle pipetting with a measuring pipette in 100 ml of HAT medium (a medium for which $10^{-4}$ mol/L hypoxanthine, $1.5\times10^{-5}$ mol/L thymidine, and $4\times10^{-7}$ mol/L aminopterin have been added to the normal medium).

A 100-µl aliquot of the suspension was dispensed into each well of a 96-well culture plate. Then the cells are cultured in an incubator with 5% $CO_2$ at 37° C. for 7 to 14 days.

After the culture is completed, an aliquot of the culture supernatant is utilized for the selection of hybridomas specifically reacting to the antigen used for the immunization according to the enzyme immuno-assay method as described in "Antibodies-A Laboratory Manual" (Cold Spring Harbor Laboratory Press, Chapter 14 (1988)), etc. to obtain the above-mentioned antibody-producing cells.

A specific example of the enzyme immuno-assay method is as follows:

An appropriate plate is coated with a purified sample of the full-length protein of the present invention or a partial fragment thereof used as an antigen for the immunization. The hybridoma culture supernatant or purified antibody obtained in (2-4) as described below is reacted as a primary antibody, and an anti-rat immunoglobulin antibody labeled with biotin, enzyme, chemically-luminescent substance, radioisotope, or the like is further reacted as a secondary antibody in the plate. Subsequently a reaction is carried out according to the label substance and cells exhibiting the specific reactivity to the protein of the present invention are selected as hybridomas producing monoclonal antibody against the protein of the present invention.

The hybridomas are cloned twice by limiting dilution method [with HT medium (HAT medium without aminopterin) in the first cloning, and with the normal medium in the second]. Cells that stably exhibit high antibody titers are selected as hybridoma lines producing monoclonal antibody against the protein of the present invention.

(2-4) Preparation of Monoclonal Antibody

The hybridoma cells obtained in (2-3) producing monoclonal antibody against the protein of the present invention are intraperitoneally injected (5 to $20\times10^6$ cells per mouse) to 8 to 10-week mice or nude mice which have been subjected to intraperitoneal administration of 0.5 ml pristane (2,6,10,14-tetramethylpentadecane) and have been bred for 2 weeks. The hybridomas form ascites carcinoma in 10 to 21 days.

The ascites is collected from each mouse having ascites tumor and then is subjected to centrifugation at 3000 rpm for 5 minutes to remove the solid material.

The monoclonal antibodies can be purified and prepared from the resulting supernatant by the same method as used for the preparation of polyclonal antibody.

Subtyping of antibody can be performed by using a typing kit for mouse or rat monoclonal antibody. The quantity of protein can be calculated according to Lowry method or by using absorbance at 280 nm.

4. Use of ICAT DNA, ICAT protein, and antibody recognizing ICAT (1) The ICAT DNA of the present invention can be used as a probe to detect or quantify mRNA of the ICAT gene in a tissue or cells by Northern blot hybridization (J. Sambrook et al. "Molecular Cloning, A Laboratory Manual, Second Edition," Cold Spring Harbor Laboratory Press (1989)) using RNA extracted from the tissue and cells. It is possible to reveal the tissue distribution of expression of ICAT by comparing the expression levels of the mRNA in a variety of tissues.

Furthermore, oligonucleotide having a nucleotide sequence identical or complementary to the nucleotide sequence of ICAT DNA of the present invention or a partial nucleotide sequence thereof can be used as a primer specific to ICAT DNA to detect or quantify the mRNA in the tissue or cells by performing RT-PCR using RNA extracted from the tissue or cells.

An oligonucleotide having a nucleotide sequence identical or complementary to the nucleotide sequence of ICAT DNA of the present invention or a partial nucleotide sequence thereof can be used as a probe to perform in situ hybridization of tissue sections for giving more detailed information on expression distribution such as identification of ICAT-expressing cells in a tissue.

Information on what tissues or cells express ICAT or information on what stimuli to the cells vary the expression level thereof, which is provided by these methods, is useful to study ICAT, for example, mechanism of signal transduction mediated by β-catenin/TCF-4 in which ICAT involved. Accordingly, these DNAs can be used as reagents for studying ICAT.

Further, there may be cancer cells having mutations which decrease the expression level of ICAT and no longer inhibit the activity of β-catenin/TCF-4 by the mutation of ICAT gene, and accordingly these DNAs can be used as diagnostic agents to assay for ICAT gene expression in such cancer.

(2) It is possible to detect abnormalities such as deletions of the ICAT gene, variation in copy number, and chromosomal translocation, and mutations in nucleotide sequence of the gene, such as substitutions, deletions, additions, etc. by using an oligonucleotide having a nucleotide sequence identical or complementary to ICAT DNA or a partial nucleotide sequence of the DNA.

Methods to detect abnormalities such as deletions, variation in copy number, and chromosomal translocation of the ICAT gene include Southern hybridization. Specifically, chromosomal DNA digested with appropriate restriction enzymes can be studied by Southern hybridization using ICAT DNA as a probe to determine abnormalities such as deletions, variation in copy number, and chromosomal translocation of the ICAT gene.

Methods to detect mutations such as substitutions, deletions, and additions in the nucleotide sequence of the ICAT gene include Southern hybridization, PCR, and SSCP (single-strand conformation polymorphism) (Proc. Natl. Acad. Sci. USA, 86, 2766 (1989)).

A mutation in the nucleotide sequence of the ICAT gene can be detected by Southern hybridization, when such a mutation, e.g., substitution, deletion, and addition, is located at a restriction enzyme site of the gene.

A mutation in the nucleotide sequence of the ICAT gene can be detected by PCR, in which the chromosomal ICAT gene is amplified by ICAT oligonucleotides to determine the nucleotide sequence of the amplified fragment.

Based on the difference in electrophoretic mobility due to nucleotide sequence alterations, a single-nucleotide difference can be detected by SSCP, in which single-stranded DNAs from the amplified fragment by PCR is electrophoresed in non-denaturing polyacrylamide gel.

When there is a mutation commonly found in cancer cells, chromosomal DNA can be analyzed by Southern hybridization using an oligonucleotide probe capable of hybridizing to the site of the mutation to diagnose such cancer.

(3) It is possible to determine the chromosomal location of the ICAT DNA by radiation-hybrid method (Science, 250, 245 (1990)) or in situ hybridization (Annals of Human Genetics, 45, 135 (1981), Cell, 52, 51 (1988)).

Radiation-hybrid method is a method for specifying precise chromosomal location, in which PCR is performed to specifically amplify the ICAT gene to many panel DNAs containing human chromosomal fragments (chromosomal positions of the fragments have been identified in the panels by using chromosomal markers) such as Gene-Bridge 4 and the result of amplification is analyzed.

In in situ hybridization, first, signals are detected after hybridizing human ICAT DNA used as a probe to a sample of human chromosome, and then the signals are mapped on the sample. This can lead to the identification of physical location of the ICAT gene on chromosome as well as the corresponding chromosome number. The probe has been labeled with radioisotope $^3$H or biotin. When $^3$H label is used, then the signal can be detected by autoradiography; alternatively when biotin label is used, it can be detected with avidin labeled with a fluorescent dye FITC.

Further, when, with an alternative method instead of the above-mentioned direct detection method for chromosomal location of the ICAT gene, an STS (sequence-tagged site: which has information on primers derived from nucleotide sequences of a variety of ESTs and chromosomal DNA fragments amplified by using the primers as well as chromosomal locations of the fragments) is found to comprise a nucleotide sequence identical to a part of the ICAT DNA by searching databases of STS for homology to the ICAT DNA nucleotide sequence, then such an STS may correspond to the ICAT gene on chromosome, and therefore chromosomal location of the STS can be presumed to correspond to the chromosomal location of the ICAT gene.

Information on the resulting identified chromosomal location of the ICAT gene can be useful to study the relation between diseases and the ICAT gene. For example, as cancer-associated chromosomal regions where the existence of tumor suppressor gene is highly possible, hot-spot regions of LOH (loss of heterozygosity: a chromosomal deletion found in one of a pair of genes) have been identified for cancer (a tumor suppressor gene is inactivated through an additional mutation of the allele on the other chromosome corresponding to the tumor suppressor gene in the region of LOH on one chromosome, which can lead to the onset of a cancer); when such a region coincides with the chromosomal location of the ICAT gene, then there is a possibility that ICAT participates in the onset of cancer having LOH in this region. In such cases, when the participation of ICAT is clarified in the cancer by analyzing mutations and expression levels of the ICAT gene, ICAT DNA and ICAT or ICAT antibody can be used to diagnose and to treat this type of cancer.

(4) ICAT can be produced and obtained by the method as described in Section 2 using ICAT DNA.

(5) In cancer cells such as colon cancer in which the APC gene, β-catenin gene, or ICAT gene has been mutated, incapability of inhibiting transcription activation by β-catenin/TCF-4 is thought to be associated with the onset of the cancer. Because ICAT can achieve the inhibition of transcription activation mediated by β-catenin/TCF-4, by the administration of ICAT, ICAT can be used as a therapeutic agent for these cancers in which inhibition of the β-catenin/TCF-4-mediated transcription activation has been impaired.

For the therapeutic agent containing the above-mentioned ICAT, the protein can be administered singly as a therapeutic agent, but typically it is preferable to provide the protein as a pharmaceutical preparation manufactured by any well-known method in the technical field of pharmaceutics after the protein is mixed with one or more pharmaceutically acceptable carriers. Preferably, a sterilized solution is used in which the protein has been dissolved in water or in an aqueous carrier such as an aqueous solution of sodium chloride, glycine, glucose, human albumin, etc. In addition, it is possible to add pharmaceutically acceptable additives such as buffering agents and isotonizing agents to be close to the physiological condition for the preparation solution as possible, for example, sodium acetate, sodium chloride, sodium lactate, potassium chloride, sodium citrate, etc. Alternatively, it is possible to freeze-dry it for the storage and then use it after dissolving it in an appropriate solvent at the time of use. It is preferable to use an administration route by which the treatment is achieved most effectively, and typically such an effective administration route is a parenteral route, for example, subcutaneous, intramuscular, intravenous, intrabronchial route, etc.

(6) It is possible to treat cancer by administering a vector for gene therapy, in which ICAT DNA has been inserted, to a patient and allowing the ICAT DNA to be expressed in target cells, instead of administrating ICAT from outside in (5).

(7) Antibodies recognizing ICAT can be produced by the method as described in Section 3 using ICAT as an antigen.

(8) ICAT can be detected by using an antibody recognizing ICAT. Specifically, the method includes a detection method such as ELISA using microtiter plates, fluorescent antibody method, Western blotting, or immunohistological staining.

(9) ICAT can be quantified by using an antibody recognizing ICAT. Specifically, such methods include sandwich ELISA using two types of monoclonal antibodies having different epitopes among antibodies capable of reacting to ICAT in liquid phase, radio-immunoasssay using ICAT labeled with a radioisotope such as $^{125}I$ and an antibody recognizing ICAT, etc.

BEST MODE FOR CARRYING OUT THE INVENTION

Figure 1:
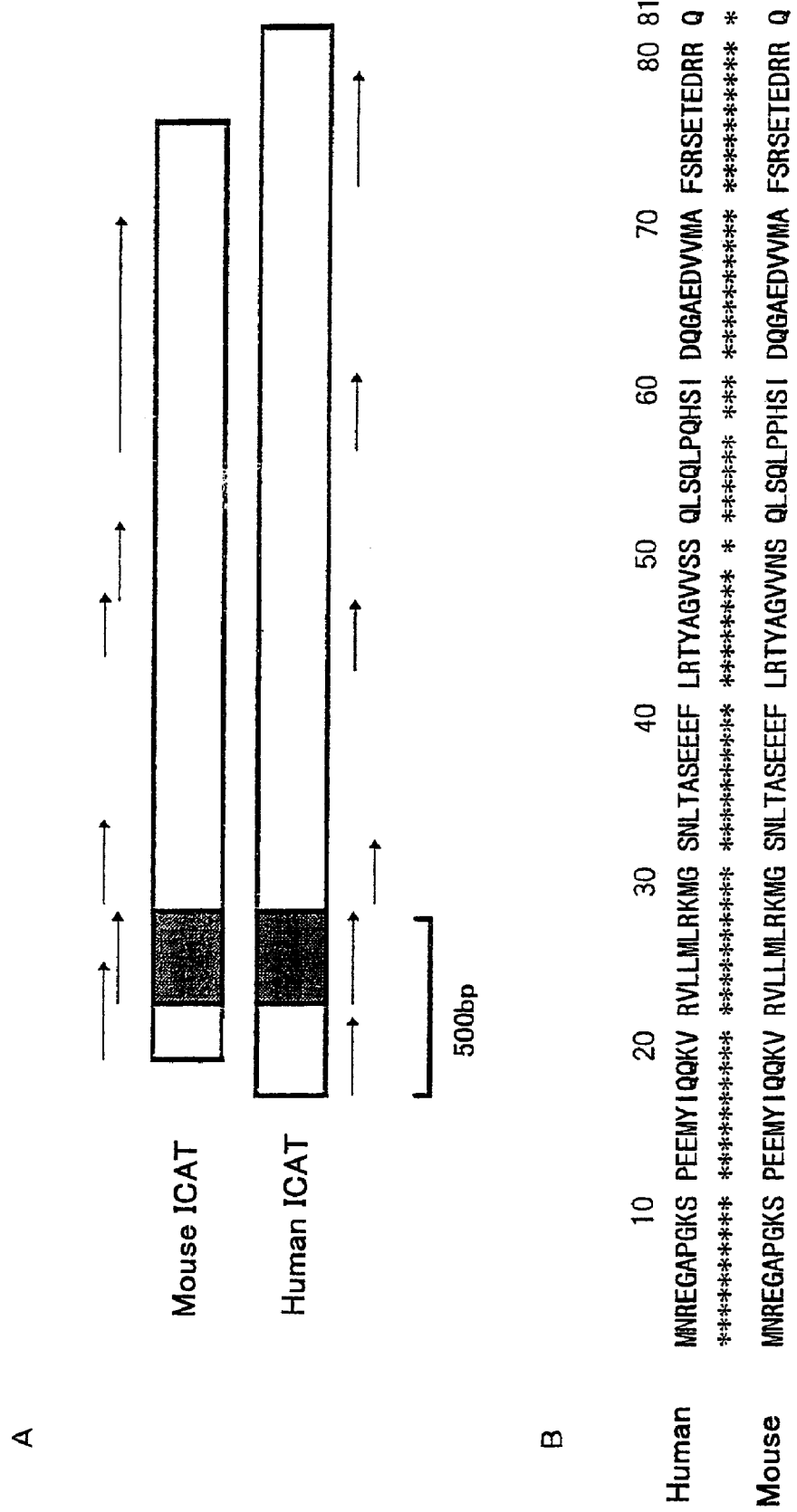
FIG. 1A indicates the positions of ORFs in the mouse ICAT cDNA and human ICAT cDNA.
FIG. 1B indicates comparison of amino acid sequence between mouse ICAT (SEQ ID NO: 4) and human ICAT (SEQ ID NO: 2).

The present invention will be described below in detail with reference to Examples.

EXAMPLE 1

Cloning of ICAT cDNA

A gene encoding a protein capable of binding to mouse mβ-catenin arm was cloned by the yeast two-hybrid system.

(1) Preparation of Bait Plasmid for mβ-Catenin Arm

The nucleotide sequence of mouse β-catenin cDNA and the amino acid sequence of mouse β-catenin encoded by the cDNA are publicly known (GenBank accession No: M90364, Science, 257, 1142 (1992)). Mouse β-catenin contains a repetitive sequence, which is called armadillo domain (mβ-catenin arm) in the region of residues 141 to 664 of its amino acid sequence. A DNA fragment of mouse β-catenin encoding this portion of mβ-catenin arm was amplified and isolated by PCR using cDNA from mouse cells as a template. The PCR primers were designed based on the nucleotide sequence of the portion of the cDNA encoding the above-mentioned mβ-catenin arm. The amplified DNA fragment was sequenced to confirm that it encodes mβ-catenin arm, and then the fragment was inserted into a vector pGBT9 (Clontech) between BamHI/SalI sites to prepare a plasmid for the expression of GAL4-β-catenin fusion protein in which β-catenin is fused with GAL4 BD.

(2) Screening Using the Two-Hybrid System

Screening was carried out with MATCHMAKER mouse fetal (Swiss Webster/NIH mouse; 17-day embryo) cDNA library, which is a library to be used for the two-hybrid system and provided by Clontech. This cDNA library contains vector pGAD10 (Clontech) with cDNA insert and as a selection marker a gene LEU2 involved in leucine biosynthesis in yeast, and can express fusion proteins between GAL4 AD and cDNA-encoding proteins by employing ADH1 promoter. Specific method for the screening used according to the manual attached to the library from Clontech is as follows.

Specifically, both mouse fetal cDNA library for the two-hybrid system and plasmid GAL4-β-catenin prepared in (1) were introduced in yeast *Saccharomyces cerevisiae* HF7C strain (Clontech). HF7C strain is a yeast strain that is tryptophan-, leucine-, and histidine-auxotrophic, and, on the chromosome, has as a reporter gene a gene involved in histidine biosynthesis, HIS3, which has been ligated downstream of GAL1 promoter to which GAL4 BD can bind, as well as has of *E. coli*-derived β-galactosidase gene lazZ ligated downstream of a nucleotide sequence where GAL4 BD can bind (Gene, 212, 197 (1998)). A transformant containing both plasmid GAL4-β-catenin and cDNA clone for protein capable of binding to mβ-catenin arm and expresses the respective fusion proteins, is non-auxotrophic for histidine and is positive in β-galactosidase activity, because GAL4 BD is placed adjacent to GAL4 AD due the binding between mβ-catenin arm and the binding protein, the transcriptions of HIS3 gene and lacZ gene, downstream of the nucleotide sequence to which GAL4 BD binds, are activated. Four clones were finally selected, as colonies positive in β-galactosidase activity from $2.3 \times 10^7$ transformants which were grown on a medium without any of leucine, histidine, and tryptophan.

Plasmid DNAs were recovered from these clones, and the nucleotide sequences were determined for the inserted cDNAs. The four clones shared the same sequence of cDNA. Nucleotide sequence databases were searched for homology to the nucleotide sequence. Although there are some nucleotide sequences of mouse ESTs identical to the sequence, no known genes were found to be identical to the nucleotide sequences. Accordingly, the above-mentioned cDNA isolated by the two-hybrid system was clarified to be a cDNA derived from a novel gene. The protein encoded by this novel gene was named ICAT.

Among the nucleotide sequences of the ESTs found, some were more extended to the 5' direction as compared with the cDNAs obtained by the two-hybrid system. Thus a sense primer for PCR was prepared based on the nucleotide sequence from the 5' end of one of these (GenBank accession No: AA017805) and further an antisense primer was prepared based on the nucleotide sequence of a mouse EST (GenBank accession No: AA253623) having the nucleotide sequence identical to the above-mentioned ICAT cDNA. A cDNA fragment containing a nucleotide sequence further extended to 5' direction was amplified by PCR using these primers and by using the mouse fetal cDNA library (Clontech) as a template and then the sequence was determined. The entire nucleotide sequence of mouse ICAT cDNA shown in SEQ ID NO: 3 was obtained by assembling the nucleotide sequence of cDNA clone prepared by the two-hybrid system and the cDNA nucleotide sequence revealed by PCR. There are multiple open reading frames (ORFs) in this nucleotide sequence. Such ORFs, which contain 50 or more amino acids, are residues 1 to 273 (91 amino acids; no initiation codon in it); residues 167 to 409 (81 amino acids); residues 447 to 647 (67 amino acids); residues 1122 to 1304 (61 amino acids), and residues 1711 to 2373 (221 amino acids) (FIG. 1A), but it was unclear which was the true ORF encoding ICAT merely based on the nucleotide sequence. Then an ORF of 81 amino acids from the most 5'-side initiation codon (SEQ ID NO: 6; which corresponds to residues 167 to 409 in the nucleotide sequence of SEQ ID NO: 1) was hypothesized as the portion encoding ICAT. The amino acid sequence of this ORF is shown in SEQ ID NO: 4 as the amino acid sequence of mouse ICAT. Homology of the amino acid sequence against amino acid sequence databases was searched, but there was no amino acid sequence with high homology.

(3) Cloning of Human ICAT cDNA

GenBank nucleotide sequence database was searched for human nucleotide sequences with homology to the nucleotide sequence of mouse ICAT cDNA obtained in (2), then it was revealed that some ESTs exhibited high homology. Further, ESTs presumed to be derived form human ICAT cDNA were collected by testing ESTs sharing sequences with these ESTs or ESTs derived from an identical clone (typically there are two ESTs of 5'-end sequence and 3'-end-sequence in a single cDNA clone), and the resulting ESTs were analyzed based on the nucleotide sequences to determine which part of human ICAT cDNA each EST corresponds to. In addition, it was estimated which part of the full-length human ICAT cDNA was contained in the cDNA clone, by determining whether the nucleotide sequences of these ESTs are located on the 5' side or 3' side of the cDNA clone that has been used for the determination of the nucleotide sequence. Based on the analytical result, ESTs of accession Nos. AA478738, W73346, and AA428913 in GenBank were selected among these ESTs, and then parental cDNA clones used for the determination of these nucleotide sequences of ESTs, namely clones IMAGE75366 (the 5'-side EST is AA478738; the cDNA clone is presumed to contain the 5' end of human ICAT cDNA), IMAGE344405 (the 3'-side EST is W73346; the cDNA clone is presumed to contain a central portion of human ICAT cDNA), and IMAGE759649 (the 5'-side EST is AA428913; the cDNA clone is presumed to contain the 3' end of human ICAT cDNA), were obtained from I.M.A.G.E. consortium. A cDNA clone phICAT, covering nearly full length of human ICAT cDNA was prepared by assembling cDNAs contained in these cDNA clones by the following method.

First, PCR was carried out by using IMAGE75366 as a template and using (a) a sense primer that has an added EcoRI site on the 5' side of the nucleotide sequence adjacent to the 5' end of the cDNA portion (specifically, which is a nucleotide sequence adjacent to the 5' end of AA478738 and corresponds to the sequence after the gth nucleotide of SEQ ID NO: 1) and (b) an antisense primer containing a PstI site located at 742$^{nd}$ residue of SEQ ID NO: 1 and nucleotide sequence downstream thereof; the amplified DNA fragment of about 760 bp was digested with EcoRI and PstI to isolate it. Then, IMAGE759649 was digested with PstI and EcoRI, and a DNA fragment containing vector pT7T3D-Pac and a 3' portion (portion after the PstI located at 980$^{th}$ residue in SEQ ID NO: 1) of human ICAT cDNA was isolated. The plasmid (sequence of residues 747 to 979 of SEQ ID NO: 1 is deleted in the cDNA of this plasmid), which had been prepared by ligating both with each other, was digested with PstI, and then the phosphate groups at the end provided by the digestion were removed by treating them with alkaline phosphatase in order to prevent self-ligation. This DNA was ligated to a DNA fragment of about 240 bp, which had been isolated after the digestion of IMAGE344405 with PstI. A plasmid clone, in which the PstI fragment had been inserted in a desired orientation, was selected as a cDNA clone containing nearly full-length human ICAT cDNA by determining the nucleotide sequence near the PstI site and then the resulting clone was named phICAT. The entire nucleotide sequence of cDNA in phICAT was determined for the nucleotide sequence of human ICAT cDNA. In this nucleotide sequence, 8 nucleotides at the 5' end of the cDNA nucleotide sequence of phICAT (corresponds to residues 1 to 8 in the nucleotide sequence of AA478738) had been removed during the process of preparing phICAT, and therefore the one in which the nucleotide sequence has been added is shown in SEQ ID NO: 1 as the nucleotide sequence of full-length human ICAT cDNA. As seen in FIG. 1A, also in this nucleotide sequence of human ICAT cDNA, there were several ORFs encoding 50 or more amino acids (residues 2 to 210 (70 amino acids; there is no initiation codon); residues 274 to 516 (81 amino acids); residues 545 to 709 (55 amino acids); residues 1206 to 1388 (61 amino acids) residues 1822 to 2025 (68 amino acids); and residues 2547 to 2864 (106 amino acids)) However, when the position of ORF within each ICAT cDNA from human and mouse and their amino acid sequences encoded by the ORFs were compared to each other, only an ORF encoding 81 amino acids corresponding to the nucleotide residues 274 to 516 of human ICAT cDNA exhibited homology to the amino acid sequence of mouse ICAT, as well as was located at a similar position to that in the mouse cDNA. The ORF corresponded to and had homology to the putative ORF encoding mouse ICAT hypothesized in (2). Accordingly, it has been revealed that the region encoding ICAT is, as was hypothesized, the region of residues 167 to 409 in SEQ ID NO: 3 (SEQ ID NO: 6) for mouse ICAT cDNA or the region of residues 274 to 516 in SEQ ID NO: 1 (SEQ ID NO: 5) for human ICAT cDNA. The nucleotide sequence of human ICAT DNA is shown in SEQ ID NO: 5 and the amino acid sequence of human ICAT is shown in SEQ ID NO: 2. Sequence comparison between the amino acid sequences of human ICAT and mouse ICAT is shown in FIG. 1B. Only a difference was 2 amino acids in 81 amino acids between human and mouse ICATs.

EXAMPLE 2

Analysis for the Expression of the ICAT Gene by Northern Blotting

Northern blotting was carried out by using as a probe mouse ICAT cDNA, which had been obtained in Example 1, labeled by random prime labeling method with an MTN BLOT (Clontech) which was a filter where poly (A)$^+$ RNAs had been blotted from various organs from adult mice (heart, brain, spleen, lung, liver, skeletal muscle, kidney, and testis) and mouse fetuses (day-7, day-11, day-15, and day-17).

Figure 2:
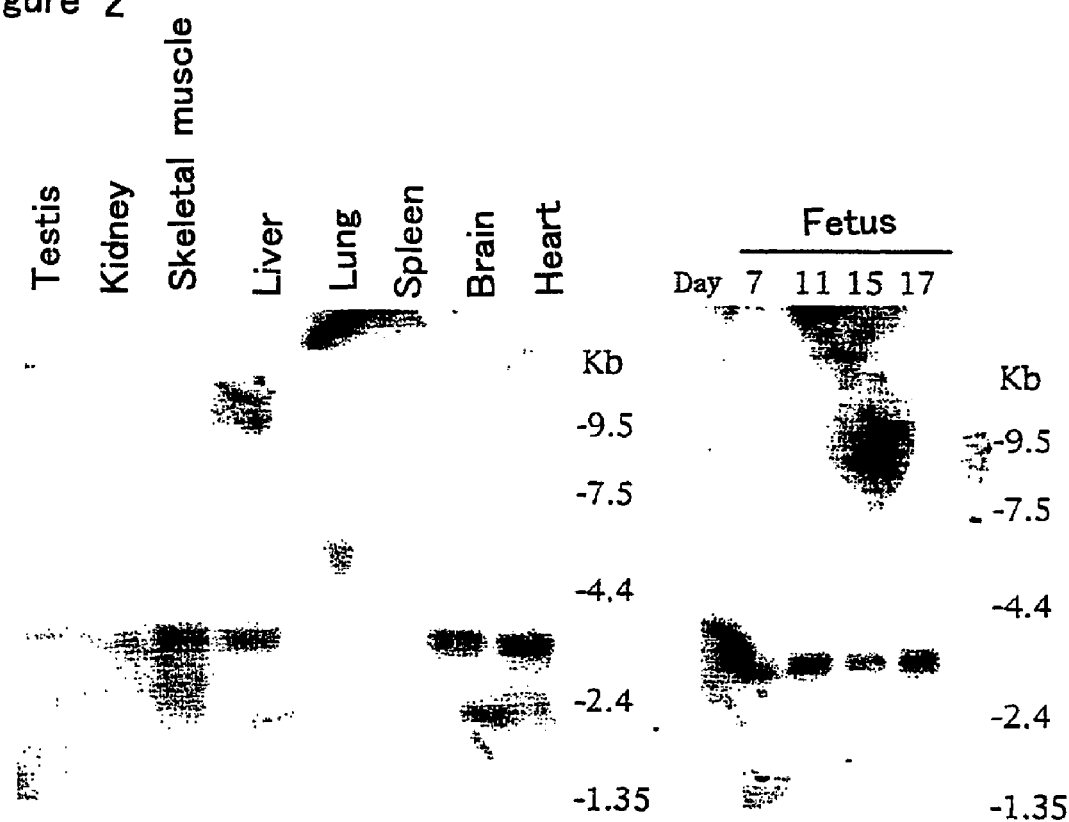
FIG. 2 indicates the results of Northern blots for ICAT mRNA in mouse tissues. From left; testis, kidney, skeletal muscle, liver, lung, spleen, brain, heart; and day-7, day-11, day-15, day-17 fetus. The numerals shown at right correspond to the positions of length markers.

The result is shown in FIG. 2. A 2.6-kb species of ICAT mRNA was detected. Among adult mouse organs, the mRNA was expressed at high levels in the heart, brain, liver, and skeletal muscle, and the level was lower in the kidney, testis, spleen, and lung. The mRNA was expressed at a same level all through the fetal stages.

EXAMPLE 3

Preparation of Anti-ICAT Antibody

A peptide (amino acid sequence: Ala Phe Ser Arg Ser Glu Thr Glu Asp Arg Arg Gln), which corresponds to residues 70 to 81 at the C-termini of the amino acid sequences of mouse and human ICATs, was synthesized by a peptide synthesizer. The peptide was conjugated with KLH by using MBS as a spacer and then used as an antigen to immunize rabbits. The immunization was performed by subcutaneous injection of 1 mg antigen in the first immunization, of 0.5 mg antigen at 10-day intervals after the second immunization. The antibody titer after the subcutaneous injection was tested by ELISA for the reactivity to the above-mentioned peptide in the sera that was collected from rabbits since the third immunization. When the titers became sufficiently high, the whole sera were collected from the rabbits to obtain anti-ICAT antisera. The anti-ICAT sera were subjected to the treatment of ammonium-sulfate precipitation and then dialyzed. The anti-ICAT polyclonal antibody was purified and obtained from the dialysate by utilizing an affinity column in which the peptide used as the antigen had been immobilized on carrier of EAH-Sepharose (Amersham-Pharmacia Biotech). The purified anti-ICAT polyclonal antibody is referred hereafter to as anti-ICAT antibody. It is shown below in Examples 4 to 7 that the antibody has specific reactivity to mouse ICAT.

EXAMPLE 4

Expression of Recombinant ICAT in *E. coli* and Detection Thereof (1) Expression of ICAT in *E. coli*

The mouse ICAT cDNA was subcloned between EcoRI/SalI sites in glutathione-5-transferase (GST) expression plasmid vector pGEX5X-1 (Amersham-Pharmacia Biotech) for *E. coli*, to prepare an expression plasmid for fusion protein in which ICAT is fused on the C-terminal side of GST (hereafter abbreviated as GST/ICAT). *E. coli* was transformed with this plasmid and then cultured. For control, *E. coli* transformed with pGEX5X-1 (this *E. coli* expresses GST alone) was also cultured.

(2) Detection of ICAT by Immunoprecipitation and Western Blotting

The transformants cultured in (1) were recovered, and then buffer A (lysis buffer A; composition of buffer A: 10 mM Tris-HCl (pH 8.0), 140 mmol/L NaCl, 1 mmol/L EGTA, 10 µg/ml leupeptin, 10 µg/ml aprotinin) containing 1% Triton X-100 was added thereto to lyse the bacteria. The cell lysate was reacted to the anti-ICAT antibody obtained in Example 3 at 4° C. for 1 hour to form immune complex between GST/ICAT and the antibody, and then protein G-Sepharose 4B (Amersham-Pharmacia Biotech), which has a property of binding to IgG, was added to the reaction solution to adsorb the immune complex. After protein G-Sepharose 4B was washed well with lysis buffer A, SDS-PAGE sample buffer was added thereto to elute the immune complex. The eluate was used as a sample in SDS-PAGE and then transferred onto PVDF membrane (Immobilon P; Millipore). The detection of ICAT was carried out with this membrane by using anti-ICAT antibody as a primary antibody and using alkaline phosphatase-conjugated anti-rabbit IgG antibody (goat) as a secondary antibody.

The result showed that a band was detected as a result of the reaction between GST/ICAT and anti-ICAT antibody in E. coli expressing GST/ICAT but no band was detected in control E. coli expressing GST. Accordingly, it has revealed that the anti-ICAT antibody obtained in Example 3 can be an antibody that specifically reacts to ICAT and is such that the detection of ICAT can be achieved in both immunoprecipitation and Western blotting.

EXAMPLE 5

Expression and Detection of Recombinant ICAT in Animal Cells

Figure 3:
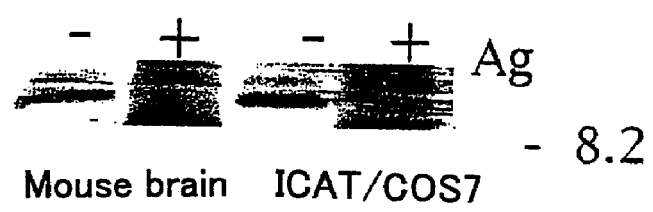
FIG. 3 indicates a result of Western blotting performed after immunoprecipitation with anti-ICAT antibody. The two lanes at left contain mouse brain extract; the two lanes at right contain the sample of COS-7 cells in which an ICAT expression vector has been introduced. Ag+ means that the lanes contain samples in which the anti-ICAT antibody was used after treated with the antigen peptide.

The mouse ICAT cDNA, which had been obtained in Example 1, was subcloned between EcoRI/SalI sites in plasmid vector pMKITneo (Nakamura et al., Genes to Cells, 3, 395 (1998)) for the expression in animal cells to prepare an ICAT expression plasmid in animal cells. The plasmid DNA was introduced into monkey kidney cell line COS-7 (ATCC: CRL-1651) with LipofectAMINE (Life Technologies). After 48 hours, the cells were recovered, cell lysate was prepared in the same manner as in Example 4, and then the detection was carried out by Western blotting after immunoprecipitation with anti-ICAT antibody. As seen in FIG. 3, the result showed that a band for 9-kDa protein was detected. The molecular weight of 9 kDa was similar to the molecular weight provided by the estimation from the amino acid sequence of ICAT. Further, when the anti-ICAT antibody was previously reacted to the partial peptide of ICAT used for the immunization and then the immunoprecipitation reaction was performed, the band of ICAT was not detected and thus the reaction between the antibody and ICAT was inhibited.

EXAMPLE 6

Synthesis of ICAT by the In-Vitro Translation System and Detection Thereof with Antibody ICAT was translated and synthesized from mouse ICAT mRNA in vitro by using TNT-reticulocyte lysate system (Promega). The synthesized was subjected to Western blotting after immunoprecipitation using anti-ICAT antibody in the same manner as in Example 4, and then a band of ICAT was detected. Accordingly, ICAT synthesized by in vitro translation system was also bound to the anti-ICAT antibody and formed immune complex.

EXAMPLE 7

Detection of ICAT in the Mouse Brain by using Antibody

The brain from a day-49 mouse was crushed in lysis buffer A with a Dounce homogenizer to prepare a lysate. The lysate was subjected to Western blotting after immunoprecipitation using anti-ICAT antibody in the same manner as in Example 4 for the detection. As seen in FIG. 3, the result showed that a band of 9-kDa protein was detected. Because a 9-kDa protein was also detected in Example 5, ICAT gene product in the brain is assumed to be the 9-kDa protein. In addition, it has revealed that the anti-ICAT antibody obtained in Example 3 is an antibody that reacts to ICAT in tissues and is an antibody such that the detection of ICAT can be achieved in both immunoprecipitation and Western blotting.

EXAMPLE 8

Analysis of Binding Between ICAT and β-catenin (1) Detection of the Direct Binding In Vitro The direct binding of ICAT to β-catenin was verified as follows. $^{35}$S-labeled β-catenin was translated and synthesized from mouse β-catenin mRNA in vitro by using $^{35}$S-labeled methionine TNT-reticulocyte lysate system (Promega). The GST/ICAT-expressing E. coli as well as control GST-expressing E. coli prepared in Example 3 were cultured to obtain the respective bacterial lysates. Glutathione-Sepharose 4B (Amersham-Pharmacia Biotech) was added to these bacterial lysates, and GSTIICAT or GST was adsorbed on it to isolate it. The GST/ICAT- or GST-adsorbed glutathione-Sepharose 4B was reacted to the above-mentioned $^{35}$S-labeled β-catenin in buffer A containing 0.1% Triton X-100 at 4° C. for 2 hours. After the glutathione-Sepharose 4B was washed well with buffer A and then SDS-PAGE sample buffer was added thereto to elute the bound protein to the sample buffer. The eluate was used as a sample in SDS-PAGE in which the gel concentration was 15% and then the gel was visualized by autoradiography. The result showed that a band of $^{35}$S-labeled β-catenin was detected for the GST/ICAT-expressing E. coli but the band was not detectable in GST-expressing E. coli. Accordingly, it has been verified that GST/ICAT directly binds to β-catenin in vitro and that the site responsible for the binding to β-catenin is located within the ICAT moiety of GST/ICAT.

(2) the Region of β-Catenin Responsible for the Binding with ICAT

Figure 4:
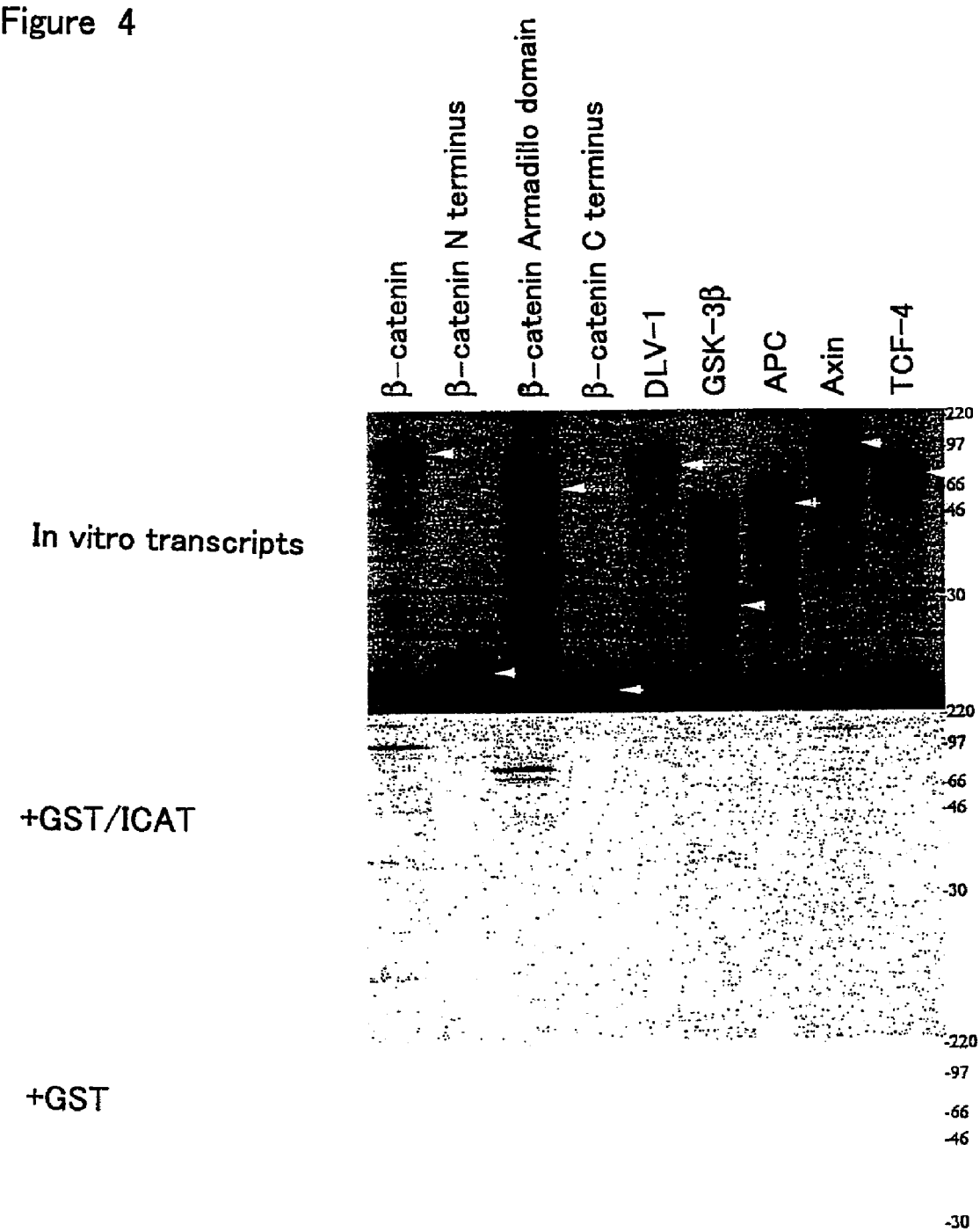
FIG. 4 indicates the binding of $^{35}S$-labeled proteins with GST/ICAT or GST. From left, the respective proteins are β-catenin, an N-terminal portion of β-catenin (amino acid sequence of residue 1 to 140), armadillo domain of β-catenin (amino acid sequence of residues 141 to 664), a C-terminal portion of β-catenin (amino acid sequence of residues 665 to 782), DVL-1, GSK-3β, APC, Axin, and TCF-4. The top panel shows a pattern of autoradiography after SDS-PAGE for products obtained in in vitro translation; the arrows represent positions of the proteins of interest. The middle panel shows a pattern of autoradiography after SDS-PAGE for fractions bound with GST/ICAT; the bottom panel, a pattern of autoradiography after SDS-PAGE for fractions bound with GST. The numerals at right represent the position of molecular weight markers in kDa.

The region of β-catenin responsible for the binding with ICAT was determined as follows. DNA fragments encoding the region of armadillo domain of mouse β-catenin (residues 141 to 664 in the amino acid sequence), N-terminal portion (residues 1 to 140 in the amino acid sequence), and C-terminal portion (residues 665 to 782 in the amino acid sequence) were amplified by PCR. By using the DNAs, mRNAs were synthesized and in vitro translated in the presence of $^{35}$S-labeled methioninein by TNT-reticulocyte lysate system (Promega) to synthesize S-labeled partial β-catenin proteins corresponding to the respective regions. The respective $^{35}$S-labeled partial β-catenin proteins were tested for the in vitro binding with GST/ICAT by immunoprecipitation in the same manner as described above. As seen in FIG. 4, while the binding with GST/ICAT was found with the armadillo domain portion, no binding was detected with N-terminal or C-terminal portion. Accordingly, it has been verified that ICAT can directly bind to the armadillo domain of β-catenin. This fact agrees with that the mouse ICAT cDNA was obtained as a DNA encoding a protein capable of binding to the armadillo domain of mouse β-catenin in Example 1.

(3) Binding Specificity of ICAT to β-Catenin

Verification that ICAT specifically binds to β-catenin was carried out as follows.

APC, DVL-1, GSK-3β, Axin, and TCF-4, which were proteins in addition to β-catenin, were synthesized in the presence of $^{35}$S-labeled methionine by in vitro translation system in the same manner as in (1) (only residues 453 to 767 of the APC amino acid sequence were synthesized as for APC). The respective $^{35}$S-labeled proteins were tested for the in vitro binding with GST/ICAT in the same manner as described above. The result is shown in FIG. 4. GST/ICAT did not bind to these proteins other than β-catenin. Accordingly, it has been revealed that the binding of ICAT is specific to β-catenin.

It has been reported that TCF-4 and δ-catenin bind to each other to form a complex. When both $^{35}$S-labeled β-catenin and $^{35}$S-labeled TCF-4 synthesized by in vitro translation system were added to the above-mentioned system and reacted with GST/ICAT, both β-catenin and TCF-4 were detected together with GST/ICAT. Accordingly, it has been shown that ICAT can directly bind to the β-catenin/TCF-4 complex (hereafter referred to as β-catenin/TCF-4).

(4) Binding Between ICAT and β-Catenin in Cells

In the experiment for the detection of ICAT with immunoprecipitation and Western blotting using COS-7 cells expressing mouse ICAT prepared in Example 5, immunoprecipitation was carried out with an anti-β-catenin monoclonal antibody (Transduction Laboratory; animal used for the immunization is mouse) instead of the anti-ICAT antibody, and Western blotting was performed with the anti-ICAT antibody as a primary antibody for the detection. The result is shown in the middle panel of FIG. 5. A band of ICAT was detected, and thus it was verified that ICAT bound to β-catenin in cells. However, when, in this experiment, the anti-β-catenin antibody, which had previously been reacted to GST/β-catenin was used in the immunoprecipitation, the band of ICAT was not detected because of inhibition of immunoprecipitation.

In the experiment for the detection of ICAT with immunoprecipitation and Western blotting using mouse brain lysate in Example 6, immunoprecipitation was carried out with the anti-ICAT antibody, and then Western blotting was performed with the anti-β-catenin monoclonal antibody (Transduction Laboratory; animal used for the immunization is mouse) as a primary antibody for the detection. As seen in the result shown in the top panel of FIG. 5, a band of β-catenin was detected, and thus it was verified that ICAT bound to β-catenin also within mouse living body. However, when, in this experiment, the anti-ICAT antibody, which had previously been reacted to GST/ICAT, was used in the immunoprecipitation, the band of β-catenin was not detected because of inhibition of immunoprecipitation.

Figure 5:
FIG. 5 indicates a result of Western blotting after the immuniprecipitation with anti-ICAT antibody or anti-β-catenin antibody. Samples are mouse brain extract in the top and bottom panels; samples used were COS-7 cells, in which ICAT expression vector had been introduced in the middle panel. The two lanes at left contain immunoprecipitates with anti-ICAT antibody; the two lanes at right contain immunoprecipitates with anti-β-catenin antibody. The top, middle, or bottom panel show Western blots, respectively using anti-β-catenin antibody, anti-ICAT antibody, or anti-TCF-4 antibody as a primary antibody.
Figure 5:
Figure 5:

Further, when, in the same experiment, Western blotting was carried out with anti-TCF-4 antibody (which is a purified antibody prepared by immunizing rabbits with a partial peptide containing an amino acid sequence corresponding to C-terminal 20 amino acids of TCF-4 in the same manner as in the preparation of the anti-ICAT antibody and then assaying the titer) as a primary antibody, then the band of TCF-4 was detected (in the bottom panel of FIG. 5). Because it has been revealed that ICAT does not directly bind to TCF-4 as shown in (3), ICAT is thought to bind to β-catenin/TCF-4 via β-catenin in mouse living body.

EXAMPLE 9

Subcellular localization of ICAT

For human colon cancer cell line SW480, ICAT and β-catenin was detected in the cells by dual fluorescent antibody method. Specifically, the cells were reacted with the anti-ICAT antibody and anti-β-catenin antibody, and then reacted with a FITC-labeled anti-rabbit IgG antibody (Cappel; which binds to the anti-ICAT antibody) and RITC-labeled anti-mouse IgG antibody (Cappel; which binds to the anti-β-catenin antibody) as secondary antibodies; ICAT and β-catenin were respectively detected in cells in a fluorescence microscope (Olympus; AH2-FL). The result showed that both ICAT and β-catenin were localized in the nucleus.

EXAMPLE 10

ICAT-Mediated Inhibition of Transcription Activation by β-Catenin and TCF

As seen in Example 8, it has been clarified that ICAT binds to β-catenin/TCF-4. β-catenin/TCF-4 has an activity of activating the transcription of target genes via binding to the target genes (the activity is hereafter referred to as the activity for transcriptional activation). Thus it was studied what influence ICAT exerted on the activity of transcriptional activation mediated by β-catenin/TCF-4. Specifically the study was carried out as follows.

β-Catenin can be phosphorylated by GSK-3β. Mutations are found at sites in β-catenin gene, which corresponds to the sites to be phosphorylated, in some colon cancer cell lines and melanoma cell lines. It has been reported that β-catenin is hardly degradable in these cell lines and thus the activity of β-catenin/TCF-4 for transcriptional activation is elevated. Thus a system was constructed to assay the activity of β-catenin/TCF-4 for transcriptional activation when a phosphorylation-free mutant β-catenin is expressed in cells by utilizing the reporter gene as shown below, and then the action of ICAT to this system was studied.

Figure 6:
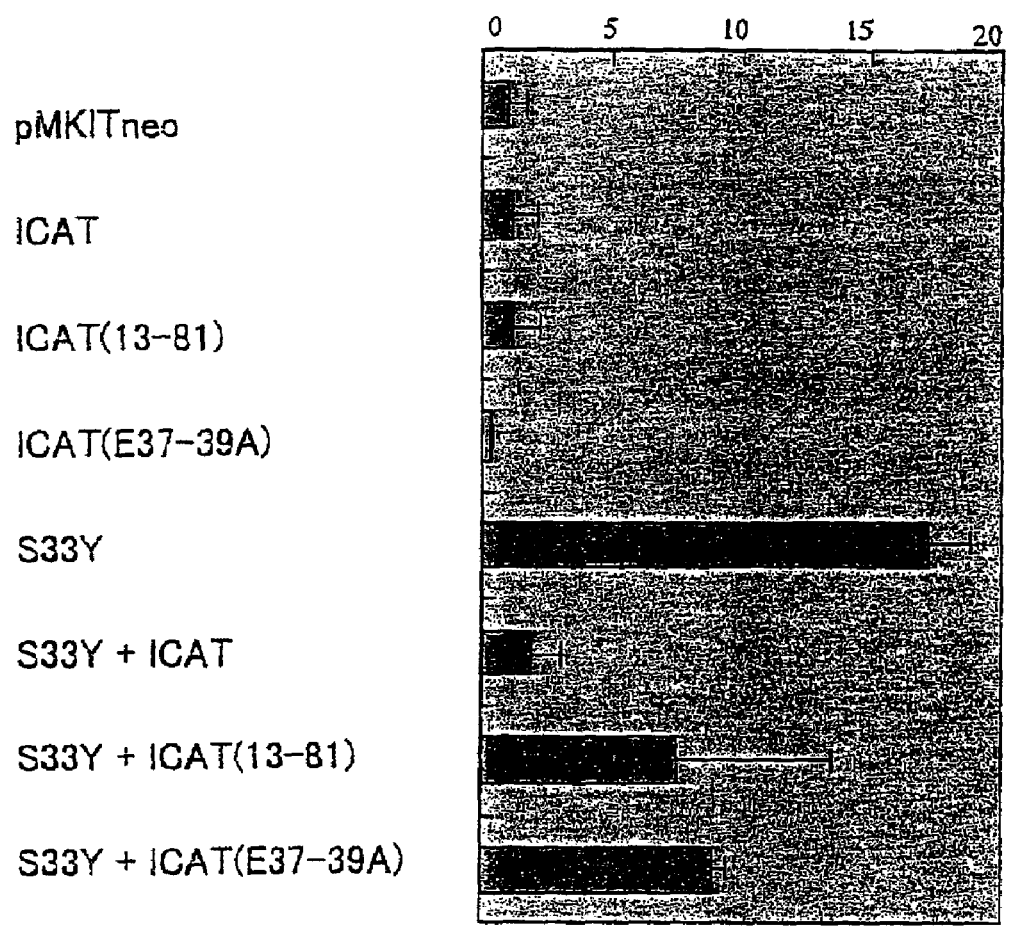
FIG. 6 indicates a result of assay for β-catenin/TCF-4-mediated transcriptional activation using a luciferase reporter plasmid, pTOPtkLuciferase in 293 cells. S33Y mutant β-catenin was not used in the 4 lanes from the top; S33Y mutant β-catenin was expressed for the remaining 4 lanes. Lanes 1 and 5 contain the control vector alone; lanes 2 and 6 contain the introduced ICAT expression vector; lanes 3 and 7 contain the introduced ICAT(13–81) expression vector; lanes 4 and 8 contain the introduced ICAT (E37–39A) expression vector.

First, a plasmid was prepared for expressing mutant β-catenin S33Y (hereafter abbreviated as S33Y) in which the 33$^{rd}$ residue serine, which is phosphorylated by GSK-3β, has been substituted with tyrosine. Then, 0.5 μg of plasmid pTOPtkLuciferase by which the luciferase gene as a reporter gene is expressed under the regulation of a promoter in which three TCF-binding sites (nucleotide sequence: CCTTTGATC) had been inserted upstream of the minimal promoter of thymidine kinase containing no regulatory sites other than the promoter (transcription activation from this promoter is affected by β-catenin/TCF-4), 1.0 μg of S33Y expression plasmid, 2.0 μg of vector MKITneo, 0.05 μg of plasmid pRL-TK (Promega) which was used a control as an index for the efficiency of gene introduction were co-transfected into 6×10$^5$ cells of human renal cell line 293 (ATCC: CRL-1573), and then the cells were cultured in a culture dish (60 mm diameter). The level of transcription directed by the promoter was estimated by assaying the activity of luciferase which is the reporter gene product 40 hours after the introduction by using a luciferase assay system kit provided by Promega. In addition, the same assay for luciferase activity was concurrently carried out for control by using 3.0 μg of MKITneo instead of S33Y expression plasmid to compare the transcriptional levels. In this comparison, the expression level by PRL-TK was used as the efficiency for gene introduction to normalize the luciferase activity. When S33Y expression plasmid was introduced, the luciferase activity, namely the transcriptional level, was confirmed to be elevated as compared with that of the control. Accordingly, it was verified that mutant β-catenin S33Y had the property of constitutively activating the transcription (FIG. 6). The same assay for the luciferase activity was conducted by using a plasmid pFOPtkLuciferase, in which the TCF-binding site contained in the above-mentioned pTOPtkLuciferase had been converted to a nucleotide sequence (CCTTTGGCC) to which TCF does not bind, as a negative control, instead of pTOPtkLuciferase. In this condition, the transcriptional level was not elevated despite the introduction of S33Y expression plasmid, and therefore the transcriptional level was verified to be elevated through the TCF-binding site.

In the assay system for the above-mentioned β-catenin/TCF-4 activity for transcriptional activation, ICAT expression plasmid was co-introduced in successively increased amount of 0, 0.1, 0.25, 0.5, or 1 μg. The increase in the amount of introduced ICAT expression plasmid DNA resulted in inhibition of elevation of transcriptional level and finally the transcriptional level reduced to the same level as in the case where vector MKITneo alone was introduced.

An assay system using mouse breast cancer cell line C57MG instead of 293 cells as a host was also prepared for the β-catenin/TCF-4 activity for transcriptional activation. The transcriptional level of the reporter gene was found to be elevated due to the introduction of S33Y expression plasmid also in this system as in the case of 293 cells. In the above-mentioned system, TCF-4 utilized was endogenous TCF-4 in the cells. However, when TCF-4 expression plasmid was additionally introduced to this system, the transcriptional level was further elevated. When ICAT expression plasmid was introduced in this assay system to express ICAT, the increase in the transcriptional level was inhibited as in the case of 293 cells. Accordingly it was verified that the action of ICAT to inhibit the β-catenin/TCF-4-mediated transcriptional activation was independent of cell type.

Figure 7:
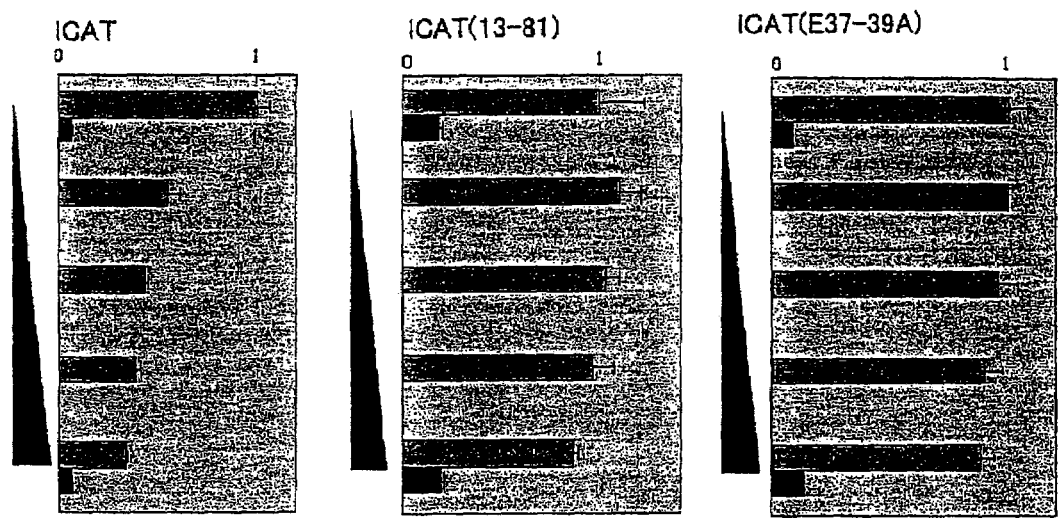
FIG. 7 indicates results of assay for β-catenin/TCF-4-associated transcriptional activation by using luciferase reporter plasmid, pTOPtkLuciferase, in DLD-1 cells (top panel) and HCT116 cells (bottom panel). The left panels show the results with the ICAT expression vector; the middle, with the ICAT(13–81) expression vector; the right, with the ICAT(E37–39A) expression vector. From the top, the result was obtained with 0, 0.1, 0.25, 0.5, or 1 µg of each ICAT or mutant ICAT expression vector.
Figure 7:
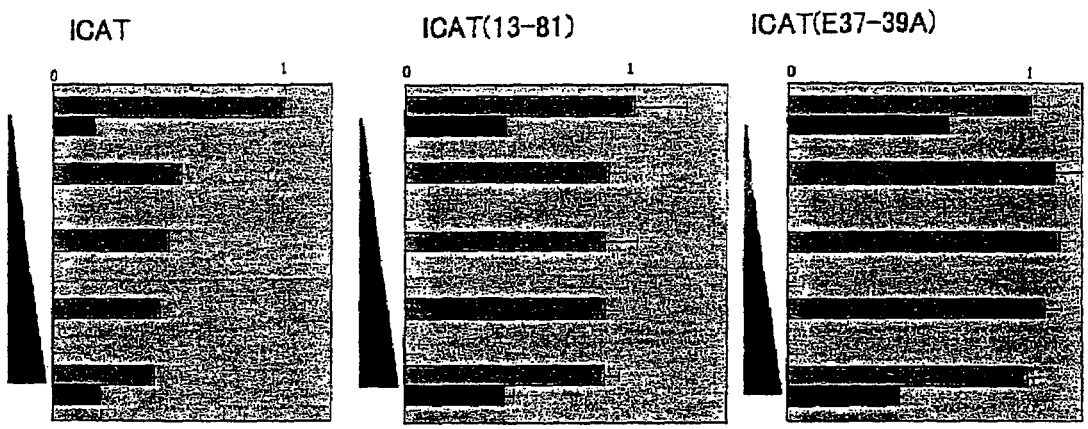

In colon cancer cell lines where APC function is impaired due to mutations of the gene, the β-catenin/TCF-4-mediated transcriptional activation is thought to constitutively occur due to the stabilization of β-catenin. Thus an assay system for the above-mentioned β-catenin/TCF-4 activity for transcriptional activation was constructed by using human colon cancer cell line, SW480(ATCC: CCL-228), DLD-1(ATCC: CCL-221), SW48(ATCC: CCL-231), or HCT116 as host cells, instead of 293 cells in the absence of S33Y expression plasmid (because constitutively activated endogenous β-catenin/TCF-4 was utilized). The ICAT expression plasmid was introduced in these systems to express ICAT, and inhibition of increase in the transcriptional level was observed as in the case described above. The result of DLD-1 and HCT116 is shown in FIG. 7. As seen in FIG. 7, it was found that ICAT also had the activity of inhibiting the transcription mediated by constitutively activated β-catenin/TCF-4 due to the presence of APC mutation.

Based on the above finding, ICAT is thought to regulate the β-catenin/TCF-4-associated signal transduction in cells via binding to β-catenin/TCF-4 in cells and inhibiting the transcription. Further, with respect to the above-mentioned assay system, forced expression of ICAT in the system where the constitutive transcriptional activation mediated by β-catenin/TCF-4 due to mutations of APC or β-catenin resulted in inhibition of the transcription. Accordingly, it is considered that cancer treatment can be achieved by administrating ICAT or by forced expression of ICAT in the cells to regulate the transcription in the cancer cells when the cancer cells have mutations of APC or β-catenin and the β-catenin/TCF-4-mediated transcriptional activation is thought to be constitutive in the cells.

EXAMPLE 11

Preparation of ICAT mutants and Evaluation of Binding Properties to β-Catenin (1) Region Associated with the Binding with β-Catenin Regions of ICAT participating in the binding with β-catenin were estimated by determining the binding between deletion mutants of ICAT and β-catenin by the two-hybrid system as follows.

Plasmids for the expression of the deletion mutants of ICAT shown below, which are expressed as GAL4 AD fusion proteins that can be utilized in the two-hybrid system, were prepared by inserting into vector pGAD424 (Clontech) partial DNA fragments encoding the respective mouse ICAT mutants amplified by PCR.

(a) ICAT (1–61); (b) ICAT(1–41); (c) ICAT (13–81); (d) ICAT(21–81); (e) ICAT (42–81); (f) ICAT (42–61); (g) ICAT (21–61); (h) ICAT(13–41); and (i) ICAT(13–61): the numerals in the parentheses correspond to amino acid numbers of the region to be expressed in the ICAT sequence); for example, ICAT(1–61) means a derivative of ICAT which contains amino acid residues 1 to 61 from the sequence.

In addition, because all of the regions responsible for the binding with β-catenin are rich in acidic amino acid in other proteins capable of binding to β-catenin, such as cadherin, APC, and TCF-4, DNA encoding an ICAT mutant ((j) ICAT(E37–39A)) of which glutamic acid residues located at residues 37, 38, and 39 were converted to alanine were amplified by PCR by utilizing a primer having a nucleotide sequence where the adenine nucleotides at the second position within the original codons (GAG or GAA) for glutamic acid residue corresponding to the residues 37, 38, and 39 have been converted to cytosine nucleotide (converted to GCG or GCA, which are codons for alanine). The DNA was inserted into vector pGAD424 (Clontech) to prepare an expression plasmid for fusion protein of GAL4 AD and ICAT(E37–39A) to be used in the two-hybrid system.

Each of these expression plasmids for fusion proteins of GAL4 AD and ICAT mutants was introduced together with the bait plasmid GAL4-β-catenin for mβ-catenin arm into yeast HF7C strain in the same manner as in Example 1, and then the binding of each ICAT mutant with β-catenin was evaluated based on the presence of β-galactosidase activity in the transformants. The result showed that (a) ICAT(1–61), (c) ICAT(13–81), and (i) ICAT(13–61) bound to β-catenin but the remaining deletion mutants did not bind to mβ-catenin arm. Accordingly, it was suggested that neither the N-terminal 12 amino acids nor the C-terminal 20 amino acids was involved in the binding, and specifically that the region of residues 13 to 61 in the amino acid sequence was important in the binding to β-catenin. In addition, (j) ICAT (E37–39A) did not bind to mβ-catenin arm. Thus, it was suggested that the consecutive glutamic acid residues 37 to 39 were important in the binding to β-catenin.

Further, ICAT(E37–39A) was expressed as a GST fusion protein in E. coli in the same manner as in Example 8 to evaluate the in vitro binding to β-catenin, and the result showed that it did not bind to β-catenin. In addition, an expression plasmid for animal cells, in which DNA encoding ICAT(E37–39A) was subcloned into vector pMKITneo, was prepared in the same manner as in Example 5, and then the plasmid was expressed in COS-7 cells. The in vivo binding to β-catenin was evaluated in the same manner as in Example 8, and the result showed that no binding was detectable. In addition, ICAT(E37–39A) was also incapable of inhibiting the β-catenin/TCF-4 activity for transcriptional activation (FIG. 7) for the case where ICAT(E37–39A) mutant was used instead of ICAT in the assay system for the β-catenin/TCF-4 activity for transcription activation as prepared in Example 10.

(2) The action of ICAT(13–81) Mutant on the β-Catenin/TCF-4-Mediated Transcriptional Activation ICAT(13–81) mutant was expressed instead of ICAT in the assay system for the β-catenin/TCF-4 activity for the transcriptional activation as prepared in Example 10.

Although this ICAT(13–81) mutant was capable of binding to β-catenin as shown in (1), the mutant could not inhibit the β-catenin/TCF-4 activity for transcriptional activation (FIG. 7). This result shows that the N-terminal 12 amino acids are important in the inhibition of β-catenin/TCF-4 activity for transcriptional activation by ICAT and that the binding to β-catenin is not enough to achieve the inhibition of β-catenin/TCF-4 activity for transcriptional activation. Further, ICAT(13–81) mutant binds to β-catenin but unlike ICAT it does not have the action of inhibiting the β-catenin-mediated transcription activation; and therefore the mutant is considered to act as an antagonist that inhibits the ICAT action antagonizing to ICAT when it is present in cells.

EXAMPLE 12

Site in β-Catenin Associated with the Binding with ICAT

The binding between mβ-catenin arm and ICAT was confirmed in Example 8. It was determined which region of mβ-catenin arm (a repetitive sequence consisting of 12 armadillo units; hereafter each repeat unit is referred to as R1 to R12) is associated with the binding to ICAT as follows.

First, DNAs encoding mβ-catenin arm truncation mutants shown below (6 types of deletion mutants containing partial mβ-catenin arm region; (a) R1 to R9, (b) R6 to R12, (c) R10 to R12, (d) the latter half of R10 to R12, (e) R10, (f) R11 to R12) were prepared by PCR, and then each were inserted into vector pGBT9 to provide the bait plasmid for the deletion mutant. The mutant was introduced together with the expression plasmid for mouse normal ICAT in the two-hybrid system into yeast HF7C strain. The binding between ICAT and mβ-catenin arm deletion mutants was evaluated based on the presence of β-galactosidase activity in the transformants. The result showed that the binding to ICAT was found when each of δ-catenin regions of (b) R6 to R12, (c) R10 to R12, or (d) the latter half of R10 to R12 was expressed, which suggested that ICAT bound to the region of the latter half of R10 to R12 of mβ-catenin arm but R1 to R9 was not involved in the binding.

EXAMPLE 13

Chromosomal Location of the Human ICAT Gene

Searching the STS database based on the nucleotide sequence of human ICAT cDNA obtained in Example 1 revealed that STSs of WI-9616, WI-16661, and SHGC-30730 had a sequence identical to that of ICAT. In addition, searching the Unigene database for EST revealed that stSG22813 and stSG2532 were STSs in this region. According to the descriptions in the databases, it has been confirmed that all the chromosomal locations of these five STSs correspond to the region between markers D1S214 and D1S244 on human chromosome 1 by some methods such as the radiation-hybrid method. The position of this marker corresponds to 1p36.1. Accordingly the human ICAT gene was considered to be located on 1p36.1 of human chromosome. There are some chromosomal deletions on 1p35–36 in neuroblastoma, melanoma, pheochromocytoma, lung cancer, liver cancer, colon cancer, and so on, and thus it is a chromosomal region where the existence of a tumor suppressor gene has been suggested (Genes Chromosomes & Cancer 16, 211, (1996)). When taking into account the fact that ICAT has the activity of inhibiting the transcription stimulation mediated by β-catenin/Tcf-4, it can be considered that ICAT acts as a tumor suppressor gene and thus is useful for the diagnosis and gene therapy for cancer.

INDUSTRIAL APPLICABILITY

A protein having activities to bind to β-catenin and to inhibit transcriptional activation induced by formation of a complex of β-catenin with a protein belonging to the TCF/Lef family, a DNA encoding the protein, an antibody recognizing the protein, a therapeutic agent containing the protein or the DNA, and a diagnostic agent containing the antibody are provided by the present invention.

---

SEQUENCE LISTING

```
<160> NUMBER OF SEQ ID NOS: 6

<210> SEQ ID NO 1
<211> LENGTH: 2997
<212> TYPE: DNA
<213> ORGANISM: Homo sapiens
<220> FEATURE:
<221> NAME/KEY: CDS
<222> LOCATION: (274)..(516)
<221> NAME/KEY: modified_base
<222> LOCATION: (2974)
<223> OTHER INFORMATION: a, t, c, g, other or unknown

<400> SEQUENCE: 1
ggccgctcct gctgctgcta ctgccgccgc cgcagcggct gctcgggctg agcacgcccc      60
ggaacaggcc gccgcgcgct gcgcgccgga cccgctgccc ctgccggccc ggccgggtcg     120
ggcggcccag ggaccgacag acttgacaac ggtgacagca ctggggcggc accttcctac     180
ttctgcccag ccacagccct cccctcacag ttgagcacct gtttgcctga agttaatttc     240
```

```
cagaagcagg agtccccaga gccaggcagg ggg atg aac cgc gag gga gct ccc      294
                                 Met Asn Arg Glu Gly Ala Pro
                                  1               5 ggg aag agt ccg gag gag atg tac att cag cag aag gtc cga gtg ctg      342
Gly Lys Ser Pro Glu Glu Met Tyr Ile Gln Gln Lys Val Arg Val Leu
         10                  15                  20 ctc atg ctg cgg aag atg gga tca aac ctg aca gcc agc gag gag gag      390
Leu Met Leu Arg Lys Met Gly Ser Asn Leu Thr Ala Ser Glu Glu Glu
     25                  30                  35 ttc ctg cgc acc tat gca ggg gtg gtc aac agc cag ctc agc cag ctg      438
Phe Leu Arg Thr Tyr Ala Gly Val Val Asn Ser Gln Leu Ser Gln Leu
 40                  45                  50                  55 cct ccg cac tcc atc gac cag ggt gca gag gac gtg gtg atg gcg ttt      486
Pro Pro His Ser Ile Asp Gln Gly Ala Glu Asp Val Val Met Ala Phe
                 60                  65                  70 tcc agg tcg gag acg gaa gac cgg agg cag tagctgcaaa gcccttggaa        536
Ser Arg Ser Glu Thr Glu Asp Arg Arg Gln
                 75                  80 cacctggat gctgttgaag ggccaagaga tctgtgtggc tcctgggccg gctgaatggc     596
agcagccccc cttgccccac ctccccctcc cctacccaac cctgccctgc ccacccccac   656
ctcacagcta ctcagtgggg ctggcatcaa gggagacacc agtggtgcgt ttataattgg   716
cttaaaggga tggacttgtg attggctgca ggaagaaact ttttttattt ttaaatcttg   776
accaacagaa acctttttatt tttatttctg actcttattt tttaaaaaat ttgcgcctcg  836
gtatctggct tccctggaag ctctccgagc tctggtgctt tagttaggtc atttttttag   896
aaatgtgaag aggtctgatt ggctgcttaa actggaaagg gactgtgatt ggctggttaa   956
tgggaaacgg ttttttttctt tggctgcagg tgttctgctg atatcaacag cttcccatt   1016
ttgaatgcag aaaacagggt ctgggacatt agtcgttata tttgacttga aagaaagaa   1076
accaagtgcg ctttgcaata tttattacac aaagaacttg ctgctgcctt cacatttggg   1136
gtttgtgttt gattggcttt cgatgcgtgt gtttggtttc ccattggttc acctgtgact   1196
cctgttgcca tggattcacc ccctctgct gccggctctg ggcctgaggg tccacctgga    1256
gagtacattt gctttaatga gtgcacctgc ctccaccagc aaggggaccc cgagaaccct   1316
gagcagggtc cacagctgga aagttgggcc cctgaggagc tttgtgtcgt cttgaacgag   1376
cagcccaggg cctagaggta accgttaggc gggatttatg tgcactgcct gcatgagctg   1436
gcaaccagcc agcgtccctt ggtgagaaag ggattgctga ggcaccgtcc aggccccacc   1496
ggccaggccg cgcccagcag aggcgtacta cccagctctg tcctcttggc catccttctg   1556
tgtaccactt cctgaggcct cattttgggg gtcatcttgg aaaggggagg agcttctccc   1616
agtgtgagac cccaaagact ctggaggtca tctggcggag gtctctggga gcccagaacc   1676
cacataaaag ccccagcttg gctcacaagg cccaggagac ctccagctaa acaccaaccc   1736
ctgacctacc ccagccaggc tcctacctgt ctgctgccag cacagtaggt cccggccagc   1796
tctggagttc tctcatcgga ggccatgcc ctccactcca ctgcctttgg aagggtctct    1856
ctccaggtca gcctggaagg gacagtatcg tttgtttatg aaatgccact gggacagctg   1916
gctgggcctt caccaagcaa gtcccttcag actggcctt aagccaaact caggcccaga    1976
attgcagttc agaatggcag tcctggaggc agggggtgag gggcaggtct agtgttcctg   2036
caccaaacct aagtccttcc acctgccacc cccttccctg ggagggaggt ggtcctccta   2096
tctccctggc tcactggcag gtgtgggatc tgggagagc ggctggagaa agatgcagtc    2156
ctcaggaagg gggccgccac cctcccctat gctggtagat gctgaggccc ctaggtgccc   2216
```

-continued

```
agggccagtg ggaccctctc agaaccaaat cttccccctt tctcggggct tggggctcgg      2276
gccgtagggg ctcctgagtg tcatgaagtg cacaggagcc aaatgaccga gccctggaga      2336
gccccatggt gggtaggtgg ttcgtgctgt gctctggcac catcagcctg ttccagaagg      2396
aggattcgag catcaggcta agaccctgtg tcctccacca tgcactcacc cctagccctg      2456
gttagctgac agtcagctgt ggggaacaca gctacaaccc taccctggca gggacctgag      2516
agcatctcag gaggggcagc gcatgtgtgc atgtgctgtg tgagtgagca cacccgtgtg      2576
cacactcata cacatgtgca cacacacgca ctctccccgc tcaggggcct ggaggtctgg      2636
ctgagcccct ggggaaaggt gagttctttc atctccctcc tccaggtcgg agtgcctgga      2696
gtcaggtgtc gaggccacat tgctggctgc cccctctttg tagctcctat aaagggccca      2756
cacctggtgg atacctggtt gagcgtgtgg tctctgcccc agcctgtcct tgtcacgatc      2816
acaggccttg cttttgtaac aatgatgacc ccggcctgtc tcatcttctg aagaggaaaa      2876
gtcaaagtgt tgctgtggct ccatatttca actaaaaata tatctgttgg agaaagaaat      2936
taacaataaa gaatttcat aggttaaaaa aaaaaaanaa aaagaaaaaa aaaaaaaaa       2996 a                                                                       2997
```

<210> SEQ ID NO 2
<211> LENGTH: 81
<212> TYPE: PRT
<213> ORGANISM: Homo sapiens

<400> SEQUENCE: 2

```
Met Asn Arg Glu Gly Ala Pro Gly Lys Ser Pro Glu Glu Met Tyr Ile
  1               5                  10                  15

Gln Gln Lys Val Arg Val Leu Leu Met Leu Arg Lys Met Gly Ser Asn
             20                  25                  30

Leu Thr Ala Ser Glu Glu Phe Leu Arg Thr Tyr Ala Gly Val Val
         35                  40                  45

Asn Ser Gln Leu Ser Gln Leu Pro Pro His Ser Ile Asp Gln Gly Ala
     50                  55                  60

Glu Asp Val Val Met Ala Phe Ser Arg Ser Glu Thr Glu Asp Arg Arg
 65                  70                  75                  80

Gln
```

<210> SEQ ID NO 3
<211> LENGTH: 2606
<212> TYPE: DNA
<213> ORGANISM: Mus musculus
<220> FEATURE:
<221> NAME/KEY: CDS
<222> LOCATION: (167)..(409)

<400> SEQUENCE: 3

```
caggccgccg cgctccggac ccgcagcccc cggcgccgcg cgttcgggcg gcccagggcg       60
gcaccttgct atttcttctc aggcgcggtc ctcccccttag agttgagcat ctgtttgcct     120
gaagtgaatt tccagaagca ggtgtcccca gaactgggcc agggg atg aac cgc         175
                                                 Met Asn Arg
                                                   1 gag gga gca ccc ggg aag agt ccg gag gag atg tac att caa cag aag      223
Glu Gly Ala Pro Gly Lys Ser Pro Glu Glu Met Tyr Ile Gln Gln Lys
        5                  10                  15 gtc cgc gtg ctg ctc atg ctg agg aag atg ggg tca aac ctg acc gcc      271
Val Arg Val Leu Leu Met Leu Arg Lys Met Gly Ser Asn Leu Thr Ala
 20                  25                  30                  35
```

| | |
|---|---|
| agt gag gag gaa ttt ctg cgc acc tat gct ggg gtc gtc agc agc cag<br>Ser Glu Glu Glu Phe Leu Arg Thr Tyr Ala Gly Val Val Ser Ser Gln<br>             40                      45                    50 | 319 |
| ctc agc cag ctg cca cag cac tcc atc gac cag ggt gca gag gac gtg<br>Leu Ser Gln Leu Pro Gln His Ser Ile Asp Gln Gly Ala Glu Asp Val<br>             55                      60                    65 | 367 |
| gtg atg gcg ttt tcc aga tcg gag acg gaa gac cgg agg cag<br>Val Met Ala Phe Ser Arg Ser Glu Thr Glu Asp Arg Arg Gln<br>             70                      75                    80 | 409 |
| tagctggaag cccctcggaa ctccctggaa gctgcagatg ccaagagat ctgtgtggct | 469 |
| cctctgccgg ttgagtggta gcaaaccacc gtcttcttac cctttgcacc ccttacccca | 529 |
| tccgaccctc cccacccagc cgccactcag cagggctggc atcaaggtgg tttgtgattg | 589 |
| gcttaaaggg atggacttga gattggctgc aggaagaaac ctttttattt ttaaatcttg | 649 |
| actaacggaa acctttatt tttatttctg actcttatt tttttaaaca tttgcgcctc | 709 |
| ggtatctggc ttccccggaa gctctccgag ctctggtgct ttatttaggt cattttagg | 769 |
| aatgtgaaga ggcctgattg gttgcttaaa ctggaaaagg gttatgattg gctggctagt | 829 |
| gggacgtggt cttttcttg attggctata gtgttctgt tcacatcacc gacttcctct | 889 |
| gttctgaaag cagaaaacgg ggtttgggat attgttatat ttgacttgaa aaaaaaaaa | 949 |
| aaagaaagaa atgaagtgag ctttgcaata tttattacac aaagagctgg ctgctgcctt | 1009 |
| cacgtagtgg gtttgtgttt ggatttgatt ggcagtaaga tgcgggtttg gtttcccatt | 1069 |
| ggctcacccc tgactcccgt tgctatggtc tttcttccac tctgctggtt acatgaggcc | 1129 |
| tgagggtaca cctggagaat gcacgtgctt taatgaccac acctgcctcc accagcgaag | 1189 |
| ggaccccagg gacgcgagcg cgagcggggt ccacagctgg agaacaggcc ccaaggggc | 1249 |
| tttgtgttct cctgagccag cagcccagag ctcaggggtg accgggaggc aggattgatg | 1309 |
| tactcagttc taagctggg cagccagcca gtttcctgga gcgaatggat tgtgcagagc | 1369 |
| tcttcaggcc tttctggcca gcccatgcta agtacaggag tgttgaccgg cagctccagc | 1429 |
| ctctctgctg ccccctgtgt ctcacttccc caggtcttgg catccccaga tcctgaaggt | 1489 |
| tatgaggggt ctttactgga gccttgaacc caagcagata ccccagtttc acttctagaa | 1549 |
| ccccagaggt ttcaaacttg gctccaagca caacctagcc aggcttccca gggtccattg | 1609 |
| ccagtggctg tagttcccgg atagcagatg tgttctacct gagcccaggc ccccattaca | 1669 |
| ccgtgtatca ccctgtgtgt cagcatagaa gggggagtag catggcttat ttattaggaa | 1729 |
| gcacccactt ggaagaccag ctagactttc acacagtagg ccccacaggc tactcagatc | 1789 |
| cagcccaagg gtcacatttt agagcagcga ctgagaagaa agatatgggt ggtcgtccca | 1849 |
| tgcccaccat gccttccctg ggagtgagag aaacggtgac ggccctttct ggtcctgggc | 1909 |
| accatgatcc ggaaaacact ggagcatctt ttcccttctt ggggcttcgg cctcccgtgt | 1969 |
| ggcagggagt gtgcaggatg ccagtgccag caggtcttga gttcaagccc tggggcacct | 2029 |
| ccctgttggt ggacggttca agcttccag acatgtccca ggaggagaat gtgaacatct | 2089 |
| ggtccctcag cacatcggcc ctgttagctg acagtaacat gctcgctttg ccattgagc | 2149 |
| tccagggagc aaggacagtg gagaatcagc tccgccaacc ccagcctgac cagcaagagc | 2209 |
| ctgagaggag agcgtcattg ctggggagga gcagcgtgtg tgagcaggca cggtatgagc | 2269 |
| tcacactgac tgacagacgc gtgcttgttc tgctggcgca gtgtggcctg gagatgtggc | 2329 |
| tgggcccgtg ggcagagatg gggtcattca gtcttcctcc cctgtgagat tgtatctaaa | 2389 |
| gtccggtgtt gccagcttca gttggttcct gtgactgcct cgaggccaag ccctggtgat | 2449 |

```
ggtgtgtgct ctgtcttagc agtggttctc ggctcagcct ctgagggaaa aagatgcaag      2509
tatcgatgtg gcttcttatt ctaactgaaa gtctatctaa tggagaaaaa aaataacaat      2569
aaagattttt cacagctaaa aaaaaaaaaa aaaaaa                                2606
```

<210> SEQ ID NO 4
<211> LENGTH: 81
<212> TYPE: PRT
<213> ORGANISM: Mus musculus

<400> SEQUENCE: 4

```
Met Asn Arg Glu Gly Ala Pro Gly Lys Ser Pro Glu Glu Met Tyr Ile
1               5                   10                  15

Gln Gln Lys Val Arg Val Leu Leu Met Leu Arg Lys Met Gly Ser Asn
            20                  25                  30

Leu Thr Ala Ser Glu Glu Glu Phe Leu Arg Thr Tyr Ala Gly Val Val
        35                  40                  45

Ser Ser Gln Leu Ser Gln Leu Pro Gln His Ser Ile Asp Gln Gly Ala
    50                  55                  60

Glu Asp Val Val Met Ala Phe Ser Arg Ser Glu Thr Glu Asp Arg Arg
65                  70                  75                  80

Gln
```

<210> SEQ ID NO 5
<211> LENGTH: 243
<212> TYPE: DNA
<213> ORGANISM: Homo sapiens
<220> FEATURE:
<221> NAME/KEY: CDS
<222> LOCATION: (1)..(243)

<400> SEQUENCE: 5

```
atg aac cgc gag gga gct ccc ggg aag agt ccg gag gag atg tac att        48
Met Asn Arg Glu Gly Ala Pro Gly Lys Ser Pro Glu Glu Met Tyr Ile
1               5                   10                  15 cag cag aag gtc cga gtg ctg ctc atg ctg cgg aag atg gga tca aac        96
Gln Gln Lys Val Arg Val Leu Leu Met Leu Arg Lys Met Gly Ser Asn
            20                  25                  30 ctg aca gcc agc gag gag gag ttc ctg cgc acc tat gca ggg gtg gtc       144
Leu Thr Ala Ser Glu Glu Glu Phe Leu Arg Thr Tyr Ala Gly Val Val
        35                  40                  45 aac agc cag ctc agc cag ctg cct ccg cac tcc atc gac cag ggt gca       192
Asn Ser Gln Leu Ser Gln Leu Pro Pro His Ser Ile Asp Gln Gly Ala
    50                  55                  60 gag gac gtg gtg atg gcg ttt tcc agg tcg gag acg gaa gac cgg agg       240
Glu Asp Val Val Met Ala Phe Ser Arg Ser Glu Thr Glu Asp Arg Arg
65                  70                  75                  80 cag                                                                   243
Gln
```

<210> SEQ ID NO 6
<211> LENGTH: 243
<212> TYPE: DNA
<213> ORGANISM: Mus musculus
<220> FEATURE:
<221> NAME/KEY: CDS
<222> LOCATION: (1)..(243)

<400> SEQUENCE: 6

```
atg aac cgc gag gga gca ccc ggg aag agt ccg gag gag atg tac att        48
Met Asn Arg Glu Gly Ala Pro Gly Lys Ser Pro Glu Glu Met Tyr Ile
1               5                   10                  15
```

-continued

| | | |
|---|---|---|
| caa cag aag gtc cgc gtg ctg ctc atg ctg agg aag atg ggg tca aac<br>Gln Gln Lys Val Arg Val Leu Leu Met Leu Arg Lys Met Gly Ser Asn<br>20                        25                   30 | | 96 |
| ctg acc gcc agt gag gag gaa ttt ctg cgc acc tat gct ggg gtc gtc<br>Leu Thr Ala Ser Glu Glu Glu Phe Leu Arg Thr Tyr Ala Gly Val Val<br>35                40                   45 | | 144 |
| agc agc cag ctc agc cag ctg cca cag cac tcc atc gac cag ggt gca<br>Ser Ser Gln Leu Ser Gln Leu Pro Gln His Ser Ile Asp Gln Gly Ala<br>50                55                   60 | | 192 |
| gag gac gtg gtg atg gcg ttt tcc aga tcg gag acg gaa gac cgg agg<br>Glu Asp Val Val Met Ala Phe Ser Arg Ser Glu Thr Glu Asp Arg Arg<br>65                70                   75                   80 | | 240 |
| cag<br>Gln | | 243 |

The invention claimed is:

1. An isolated protein comprising the amino acid sequence of SEQ ID NO: 2 or 4.

2. An isolated deletion mutant protein comprising the amino acid residue numbers 1–61 of sequences of SEQ ID NO: 2 or 4, wherein said protein has activities to bind to β-catenin and to inhibit transcriptional activation induced by formation of a complex of β-catenin with a protein belonging to the TCF/Lef family.

3. An isolated protein comprises the amino acid sequence of SEQ ID NO: 2.

4. An isolated deletion mutant protein comprising the amino acid residue numbers 1–61 of sequence of SEQ ID NO: 2, wherein said protein has activities to bind to β-catenin and to inhibit transcriptional activation induced by formation of a complex of β-catenin with a protein belonging to the TCF/Lef family.

* * * * *